(12) United States Patent
Sparling et al.

(10) Patent No.: US 7,582,730 B2
(45) Date of Patent: Sep. 1, 2009

(54) **TRANSFERRIN-BINDING PROTEINS FROM *NEISSERIA GONORRHOEAE***

(75) Inventors: P. Frederick Sparling, Moncure, NC (US); Cynthia Nau Cornelissen, Durham, NC (US)

(73) Assignee: University of North Carolina at Chapel Hill, Chapel Hill, NC (US)

( * ) Notice: Subject to any disclaimer, the term of this patent is extended or adjusted under 35 U.S.C. 154(b) by 189 days.

(21) Appl. No.: 10/928,311

(22) Filed: Aug. 30, 2004

(65) Prior Publication Data

US 2007/0065453 A1    Mar. 22, 2007

Related U.S. Application Data

(60) Continuation of application No. 09/332,226, filed on Jun. 14, 1999, now abandoned, which is a continuation of application No. 08/363,124, filed on Dec. 23, 1994, now Pat. No. 5,912,336, which is a continuation of application No. 08/124,254, filed on Sep. 20, 1993, now abandoned, which is a division of application No. 07/973,336, filed on Nov. 5, 1992, now abandoned, which is a continuation-in-part of application No. 07/572,187, filed on Aug. 23, 1990, now abandoned.

(51) Int. Cl.
*C07K 14/00*    (2006.01)
(52) U.S. Cl. ..................................... 530/350
(58) Field of Classification Search ........................ None
See application file for complete search history.

(56) References Cited

U.S. PATENT DOCUMENTS 5,141,743 A    8/1992    Schryvers et al.
5,292,869 A *  3/1994    Schryvers ................... 530/413
5,912,336 A    6/1999    Sparling et al.

FOREIGN PATENT DOCUMENTS

FR           2692592    12/1993

OTHER PUBLICATIONS

Ayala et al., Modern Genetics 45-48 (1980).
Banerjee-Bhatnagar et al., Infection and Immunity, 58(9):2875-2881 (1990).
Biswas, et al., Journal of Bacteriology, 151(2):77-82 (1982).
Black et al., Infection and Immunity 54(3):710-713 (1986).
Blanton et al., Journal of Bacteriology 172(9):5225-5235 (1990).
Brener et al., Infection and Immunity 33(1):59-66 (1981).
Dyer et al., Microbial Pathogenesis, 3:351-363 (1987).
Genius Nonradioactive DNA Labeling and Detection Kit (1989).
Gigapack Plus for packaging recombinant lambda phage (1988).
Griffiths et al., FEMS Microbiology Letters, 69:31-36 (1990).
Kohler et al., Nature 256:495-97 (1975).
Lee et al., Mol. Microbiol., 2(6):827-829 (1988).
Legrain et al., Gene, 130:73-80 (1993).
Mazarin et al., Gene, 158:145-6 (1995).
McKenna et al., Infection and Immunity, 56(4):785-791 (1988).
Ogunnariwo et al., Infection and Immunity, 58(7):2091-2097 (1990).
Old et al., Principles of Gene Manipulation 2(6):88-92 (1981).
Palmer et al., FEMS Microbiol. Lett. 110:139-146 (1993).
Paterson, Biologic and Clinical Basis of Infectious Diseases 596-609 (1980).
PicoBlue Immunoscreening Kit—Instructional Manual, (1989).
Predigested Lambda Zap/EcoRI Cloning Kit Instruction Manual, (1987).
Schryvers et al., Infection and Immunity 56(5):1144-1149 (1988).
Schryvers et al., Molecular Microbiology 281-288 (1988).
Schryvers, Molecular Microbiology 2(4):467-472 (1988).
Sims et al., Science 241:585-589 (1988).
Tsai et al., Infection and Immunity, 56(12): 3132-3138(1988).
West et al., Infection and Immunity 47(2):388-394 (1985.
West et al., Proceedings from the Fourth International Symposium, American Society of Microbiology 415-422 (1985).
Young et al., PNAS USA 80:1194-1198 (1983).

* cited by examiner

*Primary Examiner*—Olga N Chernyshev
*Assistant Examiner*—Stacey MacFarlane
(74) *Attorney, Agent, or Firm*—Averie K. Hason

(57) ABSTRACT

Iron-regulated, outer membrane proteins found in *Neisseria gonorrhoeae* and *Neisseria meningitidis* are important in transferrin receptor function. The proteins, which are isolatable by means of a transferrin affinity column, bind specifically to antisera raised against an iron-regulated outer membrane protein having a molecular weight of approximately 100 kD found in *Neisseria gonorrhoeae*.

1 Claim, 16 Drawing Sheets

Figure 1

| | | | | | | |
|---|---|---|---|---|---|---|
| AACCGCTGAA | AACAGGTCGG | AGGCAACCTT | TACCATTGAC | GCCATGATTG | AGGGCAACGG | 60 |
| CTTTAAAGGT | ACGGCGAAAA | CCGGTAATGA | CGGATTTGCG | CCGGATCAAA | ACAATAGCAC | 120 |
| CGTTACACAT | AAAGTGCACA | TCGCAAATGC | CGAAGTGCAG | GGCGGTTTTT | ACGGGCCTAA | 180 |
| CGCCGAAGAG | TTGGGCGGAT | GGTTTGCCTA | TCCGGGCAAT | GAACAAACGA | AAAATGCAAC | 240 |
| AGTTGAATCC | GGCAATGGAA | ATTCAGCAAG | CAGTGCAACT | GTCGTATTCG | GTGCGAAACG | 300 |
| CCAAAAGCTT | GTGAAATAAG | CACGGCTGCC | GAACAATCGA | GAATAAGGCT | TCAGACGGCA | 360 |
| TCGTTCCTTC | CGATTCCGTC | TGAAAGCGAA | CATTAGGGAA | ACACT ATG CAA CAG | | 414 |
| | | | | Met Gln Gln | | |
| | | | | 1 | | |

```
CAA CAT TTG TTC CGA TTA AAT ATT TTA TGC CTG TCT TTA ATG ACT GCG   462
Gln His Leu Phe Arg Leu Asn Ile Leu Cys Leu Ser Leu Met Thr Ala
      5              10                  15

CTG CCC GCT TAT GCA GAA AAT GTG CAA GCC GGA CAA GCA CAG GAA AAA   510
Leu Pro Ala Tyr Ala Glu Asn Val Gln Ala Gly Gln Ala Gln Glu Lys
 20              25                  30                      35

CAG TTG GAT ACC ATA CAG GTA AAA GCC AAA AAA CAG AAA ACC CGC CGC   558
Gln Leu Asp Thr Ile Gln Val Lys Ala Lys Lys Gln Lys Thr Arg Arg
                 40                  45                  50

GAT AAC GAA GTA ACC GGT TTG GGC AAA TTG GTC AAA ACC GCC GAC ACC   606
Asp Asn Glu Val Thr Gly Leu Gly Lys Leu Val Lys Thr Ala Asp Thr
                 55                  60                  65

CTC AGC AAG GAA CAG GTA CTC GAC ATC CGC GAC CTG ACG CGT TAC GAC   654
Leu Ser Lys Glu Gln Val Leu Asp Ile Arg Asp Leu Thr Arg Tyr Asp
             70                  75                  80

CCC GGC ATC GCC GTC GTC GAA CAG GGG CGC GGC GCA AGC TCG GGC TAC   702
Pro Gly Ile Ala Val Val Glu Gln Gly Arg Gly Ala Ser Ser Gly Tyr
         85                  90                  95

TCG ATA CGC GGT ATG GAC AAA AAC CGC GTC TCC TTG ACG GTG GAC GGC   750
Ser Ile Arg Gly Met Asp Lys Asn Arg Val Ser Leu Thr Val Asp Gly
100                 105                 110                 115
```

Figure 1.1

```
TTG GCG CAA ATA CAG TCC TAC ACC GCG CAG GCG GCA TTG GGC GGG ACG    798
Leu Ala Gln Ile Gln Ser Tyr Thr Ala Gln Ala Ala Leu Gly Gly Thr
            120                 125                 130

AGG ACG GCG GGC AGC AGC GGC GCA ATC AAT GAA ATC GAG TAT GAG AAC    846
Arg Thr Ala Gly Ser Ser Gly Ala Ile Asn Glu Ile Glu Tyr Glu Asn
            135                 140                 145

GTC AAG GCT GTC GAA ATC AGC AAA GGC TCA AAC TCG GTC GAA CAA GGC    894
Val Lys Ala Val Glu Ile Ser Lys Gly Ser Asn Ser Val Glu Gln Gly
            150                 155                 160

AGC GGC GCA TTG GCG GGC TCG GTC GCA TTT CAA ACC AAA ACC GCC GAC    942
Ser Gly Ala Leu Ala Gly Ser Val Ala Phe Gln Thr Lys Thr Ala Asp
            165                 170                 175

GAT GTT ATC GGG GAA GGC AGG CAG TGG GGC ATT CAG AGT AAA ACC GCC    990
Asp Val Ile Gly Glu Gly Arg Gln Trp Gly Ile Gln Ser Lys Thr Ala
180                 185                 190                 195

TAT TCC GGC AAA AAC CGG GGG CTT ACC CAA TCC ATC GCG CTG GCG GGG   1038
Tyr Ser Gly Lys Asn Arg Gly Leu Thr Gln Ser Ile Ala Leu Ala Gly
            200                 205                 210

CGC ATC GGC GGT GCG GAG GCT TTG CTG ATC CGC ACC GGG CGG CAC GCG   1086
Arg Ile Gly Gly Ala Glu Ala Leu Leu Ile Arg Thr Gly Arg His Ala
            215                 220                 225

GGG GAA ATC CGC GCC CAC GAA GCC GCC GGA CGC GGC GTT CAG AGC TTC   1134
Gly Glu Ile Arg Ala His Glu Ala Ala Gly Arg Gly Val Gln Ser Phe
            230                 235                 240

AAC AGG CTG GCG CCG GTT GAT GAC GGC AGC AAG TAC GCC TAT TTC ATC   1182
Asn Arg Leu Ala Pro Val Asp Asp Gly Ser Lys Tyr Ala Tyr Phe Ile
            245                 250                 255

GTT GAA GAA GAA TGC AAA AAC GGG GGT CAC GAA AAG TGT AAA GCG AAT   1230
Val Glu Glu Glu Cys Lys Asn Gly Gly His Glu Lys Cys Lys Ala Asn
260                 265                 270                 275

CCG AAA AAA GAT GTT GTC GGC GAA GAC AAA CGT CAA ACG GTT TCC ACC   1278
Pro Lys Lys Asp Val Val Gly Glu Asp Lys Arg Gln Thr Val Ser Thr
            280                 285                 290
```

Figure 1.2

```
CGA GAC TAC ACG GGC CCC AAC CGC TTC CTC GCC GAT CCG CTT TCA TAC    1326
Arg Asp Tyr Thr Gly Pro Asn Arg Phe Leu Ala Asp Pro Leu Ser Tyr
            295             300             305

GAA AGC CGG TCG TGG CTG TTC CGC CCG GGT TTT CGT TTT GAA AAC AAA    1374
Glu Ser Arg Ser Trp Leu Phe Arg Pro Gly Phe Arg Phe Glu Asn Lys
            310             315             320

CGG CAC TAC ATC GGC GGC ATA CTC GAA CGC ACG CAA CAA ACT TTC GAC    1422
Arg His Tyr Ile Gly Gly Ile Leu Glu Arg Thr Gln Gln Thr Phe Asp
            325             330             335

ACG CGC GAT ATG ACG GTT CCG GCA TTT CTG ACC AAG GCG GTT TTT GAT    1470
Thr Arg Asp Met Thr Val Pro Ala Phe Leu Thr Lys Ala Val Phe Asp
340             345             350                     355

GCA AAT CAA AAA CAG GCG GGT TCT TTG CGC GGC AAC GGC AAA TAC GCG    1518
Ala Asn Gln Lys Gln Ala Gly Ser Leu Arg Gly Asn Gly Lys Tyr Ala
            360             365             370

GGC AAC CAC AAA TAC GGC GGA CTG TTT ACC AGC GGC GAA AAC AAT GCG    1566
Gly Asn His Lys Tyr Gly Gly Leu Phe Thr Ser Gly Glu Asn Asn Ala
            375             380             385

CCG GTG GGC GCG GAA TAC GGT ACG GGC GTG TTT TAC GAC GAG ACG CAC    1614
Pro Val Gly Ala Glu Tyr Gly Thr Gly Val Phe Tyr Asp Glu Thr His
            390             395             400

ACC AAA AGC CGC TAC GGT TTG GAA TAT GTC TAT ACC AAT GCC GAT AAA    1662
Thr Lys Ser Arg Tyr Gly Leu Glu Tyr Val Tyr Thr Asn Ala Asp Lys
            405             410             415

GAC ACT TGG GCG GAT TAT GCC CGC CTC TCT TAC GAC CGG CAG GGC ATC    1710
Asp Thr Trp Ala Asp Tyr Ala Arg Leu Ser Tyr Asp Arg Gln Gly Ile
420             425             430                     435

GGT TTG GAC AAC CAT TTT CAG CAG ACG CAC TGT TCC GCC GAC GGT TCG    1758
Gly Leu Asp Asn His Phe Gln Gln Thr His Cys Ser Ala Asp Gly Ser
            440             445             450

GAC AAA TAT TGC CGT CCG AGT GCC GAC AAG CCG TTT TCC TAT TAC AAA    1806
Asp Lys Tyr Cys Arg Pro Ser Ala Asp Lys Pro Phe Ser Tyr Tyr Lys
            455             460             465
```

Figure 1.3

```
TCC GAC CGC GTG ATT TAC GGG GAA AGC CAT AAG CTC TTG CAG GCG GCA    1854
Ser Asp Arg Val Ile Tyr Gly Glu Ser His Lys Leu Leu Gln Ala Ala
        470             475                 480

TTC AAA AAA TCC TTC GAT ACC GCC AAA ATC CGC CAC AAC CTG AGC GTG    1902
Phe Lys Lys Ser Phe Asp Thr Ala Lys Ile Arg His Asn Leu Ser Val
    485             490                 495

AAT CTC GGT TAC GAC CGC TTC GGC TCT AAT CTC CGC CAT CAG GAT TAT    1950
Asn Leu Gly Tyr Asp Arg Phe Gly Ser Asn Leu Arg His Gln Asp Tyr
500             505                 510                 515

TAT TAT CAA AGT GCC AAC CGC GCC TAT TCG TTG AAA ACG CCC CCT CAA    1998
Tyr Tyr Gln Ser Ala Asn Arg Ala Tyr Ser Leu Lys Thr Pro Pro Gln
                520                 525                 530

AAC AAC GGC AAA AAA ACC AGC CCC AAC GGC AGA GAA AAG AAT CCC TAT    2046
Asn Asn Gly Lys Lys Thr Ser Pro Asn Gly Arg Glu Lys Asn Pro Tyr
            535                 540                 545

TGG GTC AGC ATA GGC AGG GGA AAT GTC GTT ACG AGG CAA ATC TGC CTC    2094
Trp Val Ser Ile Gly Arg Gly Asn Val Val Thr Arg Gln Ile Cys Leu
        550                 555                 560

TTT GGC AAC AAT ACT TAT ACG GAC TGC ACG CCG CGC AGC ATC AAC GGC    2142
Phe Gly Asn Asn Thr Tyr Thr Asp Cys Thr Pro Arg Ser Ile Asn Gly
    565                 570                 575

AAA AGC TAT TAC GCG GCG GTC CGG GAC AAT GTC CGT TTG GGC AGG TGG    2190
Lys Ser Tyr Tyr Ala Ala Val Arg Asp Asn Val Arg Leu Gly Arg Trp
580             585                 590                 595

GCG GAT GTC GGC GCG GGC TTG CGC TAC GAC TAC CGC AGC ACG CAT TCG    2238
Ala Asp Val Gly Ala Gly Leu Arg Tyr Asp Tyr Arg Ser Thr His Ser
                600                 605                 610

GAC GAC GGC AGC GTT TCC ACC GGC ACG CAC CGC ACC CTG TCC TGG AAC    2286
Asp Asp Gly Ser Val Ser Thr Gly Thr His Arg Thr Leu Ser Trp Asn
            615                 620                 625

GCC GGC ATC GTC CTC AAA CCT GCC GAC TGG CTG GAT TTG ACT TAC CGC    2334
Ala Gly Ile Val Leu Lys Pro Ala Asp Trp Leu Asp Leu Thr Tyr Arg
        630                 635                 640
```

Figure 1.4

```
ACT TCA ACC GGC TTC CGC CTG CCC TCG TTT GCG GAA ATG TAC GGC TGG   2382
Thr Ser Thr Gly Phe Arg Leu Pro Ser Phe Ala Glu Met Tyr Gly Trp
    645             650             655

CGG TCG GGC GAT AAA ATA AAA GCC GTC AAA ATC GAT CCG GAA AAA TCG   2430
Arg Ser Gly Asp Lys Ile Lys Ala Val Lys Ile Asp Pro Glu Lys Ser
660             665             670             675

TTC AAC AAA GAA GCC GGC ATC GTG TTT AAA GGC GAT TTC GGC AAC TTG   2478
Phe Asn Lys Glu Ala Gly Ile Val Phe Lys Gly Asp Phe Gly Asn Leu
                680             685             690

GAG GCA AGT TGG TTC AAC AAT GCC TAC CGC GAT TTG ATT GTC CGG GGT   2526
Glu Ala Ser Trp Phe Asn Asn Ala Tyr Arg Asp Leu Ile Val Arg Gly
                695             700             705

TAT GAA GCG CAA ATT AAA GAC GGC AAA GAA CAA GTC AAA GGC AAC CCG   2574
Tyr Glu Ala Gln Ile Lys Asp Gly Lys Glu Gln Val Lys Gly Asn Pro
    710             715             720

GCT TAC CTC AAT GCC CAA AGC GCG CGG ATT ACC GGC ATC AAT ATT TTG   2622
Ala Tyr Leu Asn Ala Gln Ser Ala Arg Ile Thr Gly Ile Asn Ile Leu
    725             730             735

GGC AAA ATC GAT TGG AAC GGC GTA TGG GAT AAA TTG CCC GAA GGT TGG   2670
Gly Lys Ile Asp Trp Asn Gly Val Trp Asp Lys Leu Pro Glu Gly Trp
740             745             750             755

TAT TCC ACA TTT GCC TAT AAT CGT GTC CGT GTC CGC GAC ATC AAA AAA   2718
Tyr Ser Thr Phe Ala Tyr Asn Arg Val Arg Val Arg Asp Ile Lys Lys
                760             765             770

CGC GCA GAC CGC ACC GAT ATT CAA TCA CAC CTG TTT GAT GCC ATC CAA   2766
Arg Ala Asp Arg Thr Asp Ile Gln Ser His Leu Phe Asp Ala Ile Gln
            775             780             785

CCC TCG CGC TAT GTC GTC GGC TCG GGC TAT GAC CAA CCG GAA GGC AAA   2814
Pro Ser Arg Tyr Val Val Gly Ser Gly Tyr Asp Gln Pro Glu Gly Lys
        790             795             800

TGG GGC GTG AAC GGT ATG CTG ACT TAT TCC AAA GCC AAG GAA ATC ACA   2862
Trp Gly Val Asn Gly Met Leu Thr Tyr Ser Lys Ala Lys Glu Ile Thr
    805             810             815
```

Figure 1.5

```
GAG TTG TTG GGC AGC CGG GCT TTG CTC AAC GGC AAC AGC CGC AAT ACA    2910
Glu Leu Leu Gly Ser Arg Ala Leu Leu Asn Gly Asn Ser Arg Asn Thr
820             825             830             835

AAA GCC ACC GCG CGC CGT ACC CGC CCT TGG TAT ATT GTG GAC GTG TCC    2958
Lys Ala Thr Ala Arg Arg Thr Arg Pro Trp Tyr Ile Val Asp Val Ser
                840             845             850

GGT TAT TAC ACG GTT AAA AAA CAC TTC ACC CTC CGT GCG GGC GTG TAC    3006
Gly Tyr Tyr Thr Val Lys Lys His Phe Thr Leu Arg Ala Gly Val Tyr
            855             860             865

AAC CTC CTC AAC CAC CGC TAT GTT ACT TGG GAA AAT GTG CGG CAA ACT    3054
Asn Leu Leu Asn His Arg Tyr Val Thr Trp Glu Asn Val Arg Gln Thr
        870             875             880

GCC GCC GGC GCA GTC AAC CAA CAC AAA AAT GTC GGC GTT TAC AAC CGA    3102
Ala Ala Gly Ala Val Asn Gln His Lys Asn Val Gly Val Tyr Asn Arg
                885             890             895

TAT GCC GCC CCC GGC CGC AAC TAC ACA TTT AGC TTG GAA ATG AAG TTC    3150
Tyr Ala Ala Pro Gly Arg Asn Tyr Thr Phe Ser Leu Glu Met Lys Phe
900             905             910             915

TAAACGTCCG AACGCCGCAA ATGCCGTCTG AAAGGCTTCA GACGGCGTTT             3200

TTTTTACACA ATCCCCACCG TTTCCCATCC TTCCCGATAC ACCGTAATCC             3250

CGAAACCCGT CATTCCCGCG CAGGCGTGCA TCCGGG                            3286
```

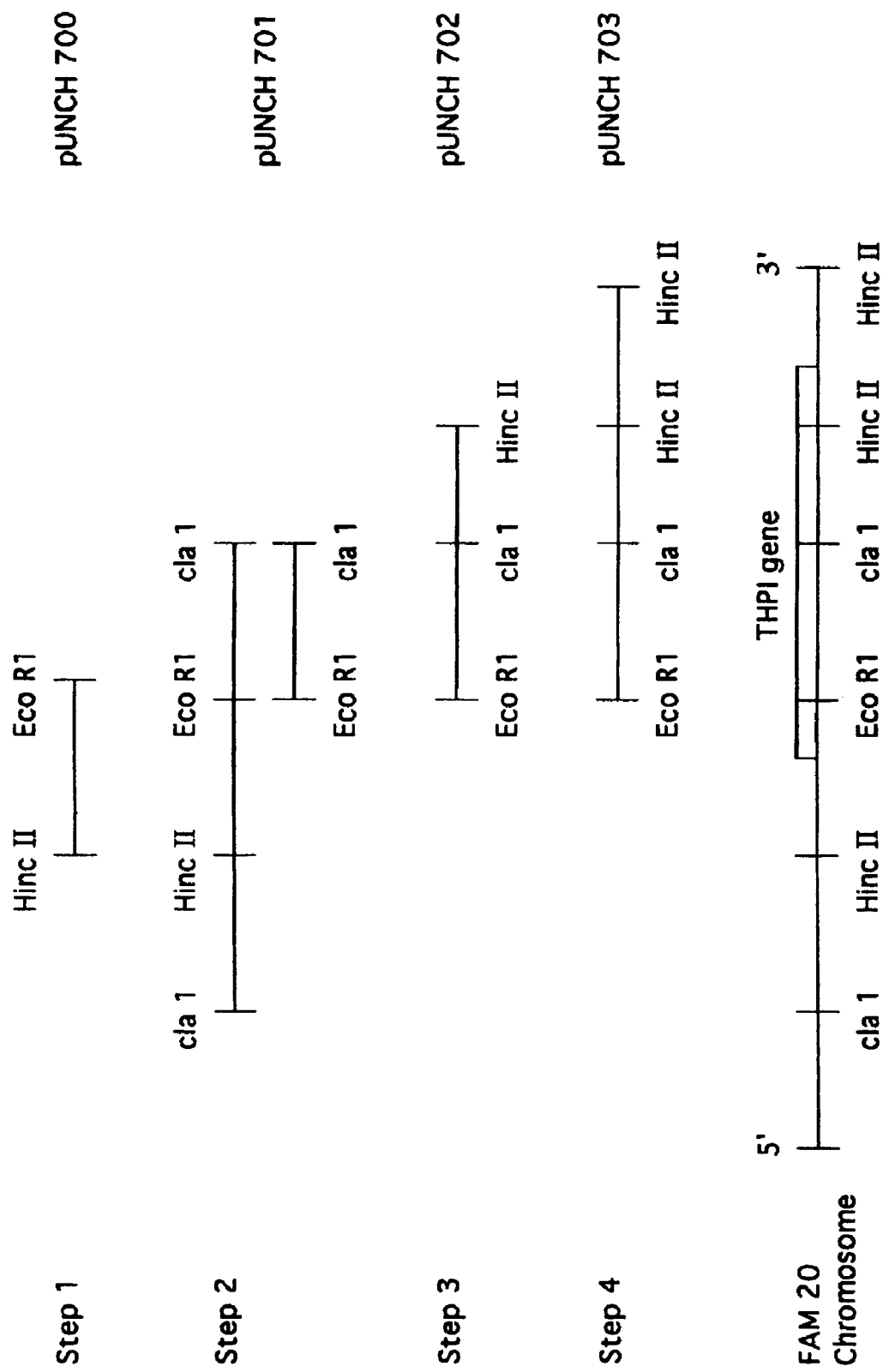

Figure 5

```
GAATTCCGAC GGAGTGGAGC TTTCACTGCT GCCGTCTGAG GGCAATAAGG CGGCATTTCA 060

GCACGAGATT GAGCAAAACG GCGTGAAGGC AACGGTGTGT TGTTCCAACT TGGATTACAT 120

GAGTTTTGGG AAGCTGTCAA AAGAAAATAA AGACGATATG TTCCTGCAAG GTGTCCGCAC 180

TCCAGTATCC GATGTGGCGG CAAGGACGGA GCAAACGCCA AATATCGCGG TACTTGGTAC 240

GGATATATTG CCAACGGCAC AAGCTGGAGC GCGAAGCCTC CAATCAGGAA GGTGGTAATA 300

GGGCAGAGTT TGACGTGGAT TTTTCCACTA AAAAAATCAG TGGCACACTG ACGGCAAAAG 360

ACCGTACGTC TCCTGCGTTT ACTATTACTG CCATGATTAA GGACAACGGT TTTTCAGGTG 420

TGGCGAAAAC CGGTGAAAAC GGCTTTGCGC TGGATCCGCA AAATACCGGA AATTCCCACT 480

ATACGCATAT TGAAGCCACT GTATCCGGCG GTTTCTACGG CAAAAACGCC ATCGAGATGG 540

CGGATCGTTC TCATTTCCGG GAAATGCACC AGAGGGAAAA CAAGAAAAAG CATCGGTGGT 600

ATTCGGTCGG AAACGCCAAC AGCTTGTGCA ATAAGCACGG CTGCCGAACA ATCGAGAATA 660

AGGCTTCAGA CGGCACCGTT CCTTCCGATG CCGTCTGAAA GCGAAGATTA GGGAAACACT 720
```

| ATG | CAA | CAG | CAA | CAT | TTG | TTC | CGA | TTA | AAT | ATT | TTA | TGC | CTG | TCT | TTA | 768 |
|---|---|---|---|---|---|---|---|---|---|---|---|---|---|---|---|---|
| Met | Gln | Gln | Gln | His | Leu | Phe | Arg | Leu | Asn | Ile | Leu | Cys | Leu | Ser | Leu | |
| -24 | | | | -20 | | | | | -15 | | | | | -10 | | |

| ATG | ACC | GCG | CTG | CCC | GTT | TAT | GCA | GAA | AAT | GTG | CAA | GCC | GAA | CAA | GCA | 816 |
|---|---|---|---|---|---|---|---|---|---|---|---|---|---|---|---|---|
| Met | Thr | Ala | Leu | Pro | Val | Tyr | Ala | Glu | Asn | Val | Gln | Ala | Glu | Gln | Ala | |
| | | | | -5 | | | | | 1 | | | | | 5 | | |

| CAG | GAA | AAA | CAG | TTG | GAT | ACC | ATA | CAG | GTA | AAA | GCC | AAA | AAA | CAG | AAA | 864 |
|---|---|---|---|---|---|---|---|---|---|---|---|---|---|---|---|---|
| Gln | Glu | Lys | Gln | Leu | Asp | Thr | Ile | Gln | Val | Lys | Ala | Lys | Lys | Gln | Lys | |
| | | 10 | | | | | 15 | | | | | 20 | | | | |

| ACC | CGC | CGC | GAT | AAC | GAA | GTA | ACC | GGG | CTG | GGC | AAG | TTG | GTC | AAG | TCT | 912 |
|---|---|---|---|---|---|---|---|---|---|---|---|---|---|---|---|---|
| Thr | Arg | Arg | Asp | Asn | Glu | Val | Thr | Gly | Leu | Gly | Lys | Leu | Val | Lys | Ser | |
| 25 | | | | | | 30 | | | | | 35 | | | | 40 | |

| TCC | GAT | ACG | CTA | AGT | AAA | GAA | CAG | GTT | TTG | AAT | ATC | CGA | GAC | CTG | ACC | 960 |
|---|---|---|---|---|---|---|---|---|---|---|---|---|---|---|---|---|
| Ser | Asp | Thr | Leu | Ser | Lys | Glu | Gln | Val | Leu | Asn | Ile | Arg | Asp | Leu | Thr | |
| | | | | 45 | | | | | 50 | | | | | 55 | | |

Figure 5.1

| | | | | | | | | | | | | | | | | |
|---|---|---|---|---|---|---|---|---|---|---|---|---|---|---|---|---|
| CGT | TAT | GAT | CCG | GGT | ATT | GCC | GTG | GTC | GAA | CAG | GGT | CGG | GGC | GCA | AGT | 1008 |
| Arg | Tyr | Asp | Pro | Gly | Ile | Ala | Val | Val | Glu | Gln | Gly | Arg | Gly | Ala | Ser | |
| | | | 60 | | | | 65 | | | | | 70 | | | | |
| TCC | GGC | TAT | TCA | ATA | CGC | GGC | ATG | GAT | AAA | AAC | CGC | GTT | TCC | TTA | ACG | 1056 |
| Ser | Gly | Tyr | Ser | Ile | Arg | Gly | Met | Asp | Lys | Asn | Arg | Val | Ser | Leu | Thr | |
| | | 75 | | | | | 80 | | | | | 85 | | | | |
| GTA | GAC | GGC | GTT | TCG | CAA | ATA | CAG | TCC | TAC | ACC | GCG | CAG | GCG | GCA | TTG | 1104 |
| Val | Asp | Gly | Val | Ser | Gln | Ile | Gln | Ser | Tyr | Thr | Ala | Gln | Ala | Ala | Leu | |
| | 90 | | | | 95 | | | | | 100 | | | | | | |
| GGT | GGG | ACG | AGG | ACG | GCG | GGT | AGC | AGC | GGC | GCA | ATC | AAT | GAA | ATC | GAG | 1152 |
| Gly | Gly | Thr | Arg | Thr | Ala | Gly | Ser | Ser | Gly | Ala | Ile | Asn | Glu | Ile | Glu | |
| 105 | | | | 110 | | | | | 115 | | | | | 120 | | |
| TAT | GAA | AAC | GTC | AAG | GCC | GTT | GAA | ATC | AGC | AAG | GGT | TCG | AAT | TCA | TCA | 1200 |
| Tyr | Glu | Asn | Val | Lys | Ala | Val | Glu | Ile | Ser | Lys | Gly | Ser | Asn | Ser | Ser | |
| | | | | 125 | | | | | 130 | | | | | 135 | | |
| GAA | TAC | GGA | AAC | GGC | GCA | TTG | GCA | GGT | TCG | GTC | GCA | TTT | CAA | ACC | AAA | 1248 |
| Glu | Tyr | Gly | Asn | Gly | Ala | Leu | Ala | Gly | Ser | Val | Ala | Phe | Gln | Thr | Lys | |
| | | | 140 | | | | | 145 | | | | | 150 | | | |
| ACC | GCA | GCC | GAC | ATT | ATC | GGA | GAG | GGA | AAA | CAG | TGG | GGC | ATT | CAG | AGT | 1296 |
| Thr | Ala | Ala | Asp | Ile | Ile | Gly | Glu | Gly | Lys | Gln | Trp | Gly | Ile | Gln | Ser | |
| | | 155 | | | | | 160 | | | | | 165 | | | | |
| AAA | ACT | GCC | TAT | TCG | GGA | AAA | GAC | CAT | GCC | CTG | ACG | CAA | TCC | CTT | GCG | 1344 |
| Lys | Thr | Ala | Tyr | Ser | Gly | Lys | Asp | His | Ala | Leu | Thr | Gln | Ser | Leu | Ala | |
| | 170 | | | | | 175 | | | | | 180 | | | | | |
| CTT | GCC | GGA | CGC | AGC | GGC | GGC | GCG | GAA | GCC | CTC | CTT | ATT | TAT | ACT | AAA | 1392 |
| Leu | Ala | Gly | Arg | Ser | Gly | Gly | Ala | Glu | Ala | Leu | Leu | Ile | Tyr | Thr | Lys | |
| 185 | | | | | 190 | | | | | 195 | | | | | 200 | |
| CGG | CGG | GGT | CGG | GAA | ATC | CAT | GCG | CAT | AAA | GAT | GCC | GGC | AAG | GGT | GTG | 1440 |
| Arg | Arg | Gly | Arg | Glu | Ile | His | Ala | His | Lys | Asp | Ala | Gly | Lys | Gly | Val | |
| | | | | 205 | | | | | 210 | | | | | 215 | | |
| CAG | AGC | TTC | AAC | CGG | CTG | GTG | TTG | GAC | GAG | GAC | AAG | AAG | GAG | GGT | GGC | 1488 |
| Gln | Ser | Phe | Asn | Arg | Leu | Val | Leu | Asp | Glu | Asp | Lys | Lys | Glu | Gly | Gly | |
| | | | 220 | | | | | 225 | | | | | 230 | | | |

Figure 5.2

```
AGT CAG TCA GAT ATT TCA TTG TGC GAA GAA GAA TGC CAC AAT GGA TAT   1536
Ser Gln Ser Asp Ile Ser Leu Cys Glu Glu Glu Cys His Asn Gly Tyr
        235             240             245

GCG GCC TGT AAA AAC AAG CTG AAA GAA GAT GCC TCG GTC AAA GAT GAG   1584
Ala Ala Cys Lys Asn Lys Leu Lys Glu Asp Ala Ser Val Lys Asp Glu
        250             255             260

CGC AAA ACC GTC AGC ACG CAG GAT TAT ACC GGC TCC AAC CGC TTA CTT   1632
Arg Lys Thr Val Ser Thr Gln Asp Tyr Thr Gly Ser Asn Arg Leu Leu
265             270             275             280

GCG AAC CCG CTT GAG TAT GGC AGC CAA TCA TGG CTG TTC CGA CCG GGT   1680
Ala Asn Pro Leu Glu Tyr Gly Ser Gln Ser Trp Leu Phe Arg Pro Gly
        285             290             295

TGG CAT TTG GAC AAC CGC CAT TAT GTC GGA GCC GTT CTC GAA CGT ACG   1728
Trp His Leu Asp Asn Arg His Tyr Val Gly Ala Val Leu Glu Arg Thr
        300             305             310

CAG CAG ACC TTT GAT ACA CGG GAT ATG ACT GTT CCT GCC TAT TTT ACC   1776
Gln Gln Thr Phe Asp Thr Arg Asp Met Thr Val Pro Ala Tyr Phe Thr
        315             320             325

AGT GAA GAT TAT GTA CCC GGT TCG CTG AAA GGT CTT GGC AAA TAT TCG   1824
Ser Glu Asp Tyr Val Pro Gly Ser Leu Lys Gly Leu Gly Lys Tyr Ser
        330             335             340

GGC GAT AAT AAG GCA GAA AGG CTG TTT GTT CAG GGA GAG GGC AGT ACA   1872
Gly Asp Asn Lys Ala Glu Arg Leu Phe Val Gln Gly Glu Gly Ser Thr
345             350             355             360

TTG CAG GGT ATC GGT TAC GGT ACC GGC GTG TTT TAT GAT GAA CGC CAT   1920
Leu Gln Gly Ile Gly Tyr Gly Thr Gly Val Phe Tyr Asp Glu Arg His
            365             370             375

ACT AAA AAC CGC TAC GGG GTC GAA TAT GTT TAC CAT AAT GCT GAT AAG   1968
Thr Lys Asn Arg Tyr Gly Val Glu Tyr Val Tyr His Asn Ala Asp Lys
        380             385             390

GAT ACC TGG GCC GAT TAC GCC CGA CTT TCT TAT GAC CGG CAA GGT ATA   2016
Asp Thr Trp Ala Asp Tyr Ala Arg Leu Ser Tyr Asp Arg Gln Gly Ile
        395             400             405
```

Figure 5.3

```
GAT TTG GAC AAC CGT TTG CAG CAG ACG CAT TGC TCT CAC GAC GGT TCG   2064
Asp Leu Asp Asn Arg Leu Gln Gln Thr His Cys Ser His Asp Gly Ser
    410                 415                 420

GAT AAA AAT TGC CGT CCC GAC GGC AAT AAA CCG TAT TCT TTC TAT AAA   2112
Asp Lys Asn Cys Arg Pro Asp Gly Asn Lys Pro Tyr Ser Phe Tyr Lys
425                 430                 435                 440

TCC GAC CGG ATG ATT TAT GAA GAA AGC CGA AAC CTG TTC CAA GCA GTA   2160
Ser Asp Arg Met Ile Tyr Glu Glu Ser Arg Asn Leu Phe Gln Ala Val
                445                 450                 455

TTT AAA AAG GCA TTT GAT ACG GCC AAA ATC CGT CAC AAT TTG AGT ATC   2208
Phe Lys Lys Ala Phe Asp Thr Ala Lys Ile Arg His Asn Leu Ser Ile
            460                 465                 470

AAT CTA GGG TAC GAC CGC TTT AAG TCG CAA TTG TCC CAC AGC GAT TAT   2256
Asn Leu Gly Tyr Asp Arg Phe Lys Ser Gln Leu Ser His Ser Asp Tyr
        475                 480                 485

TAT CTT CAA AAC GCA GTT CAG GCA TAT GAT TTG ATA ACC CCG AAA AAG   2304
Tyr Leu Gln Asn Ala Val Gln Ala Tyr Asp Leu Ile Thr Pro Lys Lys
    490                 495                 500

CCT CCG TTT CCC AAC GGA AGC AAA GAC AAC CCG TAT AGG GTG TCT ATC   2352
Pro Pro Phe Pro Asn Gly Ser Lys Asp Asn Pro Tyr Arg Val Ser Ile
505                 510                 515                 520

GGC AAG ACC ACG GTC AAT ACA TCG CCG ATA CCT GGT TTC GGC AAT AAC   2400
Gly Lys Thr Thr Val Asn Thr Ser Pro Ile Pro Gly Phe Gly Asn Asn
                525                 530                 535

ACC TAT ACA GAC TGC ACA CCG AGG AAT ATC GGC GGC AAC GGT TAT TAT   2448
Thr Tyr Thr Asp Cys Thr Pro Arg Asn Ile Gly Gly Asn Gly Tyr Tyr
            540                 545                 550

GCA GCC GTT CAA GAC AAT GTC CGT TTG GGC AGG TGG GCG GAT GTC GGA   2496
Ala Ala Val Gln Asp Asn Val Arg Leu Gly Arg Trp Ala Asp Val Gly
        555                 560                 565

GCA GGC ATA CGT TAC GAT TAC CGC AGC ACG CAT TCG GAA GAT AAG AGT   2544
Ala Gly Ile Arg Tyr Asp Tyr Arg Ser Thr His Ser Glu Asp Lys Ser
    570                 575                 580
```

Figure 5.4

```
GTC TCT ACC GGC ACT CAC CGC AAC CTT TCT TGG AAC GCG GGC GTA GTC    2592
Val Ser Thr Gly Thr His Arg Asn Leu Ser Trp Asn Ala Gly Val Val
585             590             595                 600

CTC AAA CCT TTC ACC TGG ATG GAT TTG ACT TAT CGC GCT TCT ACG GGC    2640
Leu Lys Pro Phe Thr Trp Met Asp Leu Thr Tyr Arg Ala Ser Thr Gly
            605             610             615

TTC CGT CTG CCG TCG TTT GCC GAA ATG TAT GGC TGG AGA GCC GGG GAG    2688
Phe Arg Leu Pro Ser Phe Ala Glu Met Tyr Gly Trp Arg Ala Gly Glu
            620             625             630

TCT TTG AAA ACG TTG GAT CTG AAA CCG GAA AAA TCC TTT AAT AGA GAG    2736
Ser Leu Lys Thr Leu Asp Leu Lys Pro Glu Lys Ser Phe Asn Arg Glu
            635             640             645

GCA GGT ATT GTA TTT AAA GGG GAC TTC GGC AAT TTG GAA GCC AGC TAT    2784
Ala Gly Ile Val Phe Lys Gly Asp Phe Gly Asn Leu Glu Ala Ser Tyr
            650             655             660

TTC AAC AAT GCC TAT CGC GAC CTG ATT GCA TTC GGT TAT GAA ACC CGA    2832
Phe Asn Asn Ala Tyr Arg Asp Leu Ile Ala Phe Gly Tyr Glu Thr Arg
665             670             675             680

ACT CAA AAC GGG CAA ACT TCG GCT TCT GGC GAC CCC GGA TAC CGA AAT    2880
Thr Gln Asn Gly Gln Thr Ser Ala Ser Gly Asp Pro Gly Tyr Arg Asn
            685             690             695

GGC CCA AAA TGC ACG GTA GTA GCC GGT ATC AAT ATT TTG GGT AAA ATC    2928
Gly Pro Lys Cys Thr Val Val Ala Gly Ile Asn Ile Leu Gly Lys Ile
            700             705             710

GAT TGG CAC GGC GTA TGG GGC GGG TTG CCG GAC GGG TTG TAT TCC ACG    2976
Asp Trp His Gly Val Trp Gly Gly Leu Pro Asp Gly Leu Tyr Ser Thr
            715             720             725

CTT GCC TAT AAC CGT ATC AAG GTC AAA GAT GCC GAT ATA CGC GCC GAC    3024
Leu Ala Tyr Asn Arg Ile Lys Val Lys Asp Ala Asp Ile Arg Ala Asp
            730             735             740

AGG ACG TTT GTA ACT TCA TAT CTC TTT GAT GCC GTC CAA CCT TCA CGA    3072
Arg Thr Phe Val Thr Ser Tyr Leu Phe Asp Ala Val Gln Pro Ser Arg
745             750             755             760
```

Figure 5.5

| | | | | | | | | | | | | | | |
|---|---|---|---|---|---|---|---|---|---|---|---|---|---|---|
| TAT | GTA | TTG | GGT | TTG | GGT | TAC | GAC | CAT | CCT | GAC | GGA | ATA | TGG | GGC | ATC | 3120
| Tyr | Val | Leu | Gly | Leu | Gly | Tyr | Asp | His | Pro | Asp | Gly | Ile | Trp | Gly | Ile |
| | | | 765 | | | | | 770 | | | | | 775 | | |

```
TAT GTA TTG GGT TTG GGT TAC GAC CAT CCT GAC GGA ATA TGG GGC ATC    3120
Tyr Val Leu Gly Leu Gly Tyr Asp His Pro Asp Gly Ile Trp Gly Ile
            765             770             775

AAT ACG ATG TTT ACT TAT TCC AAG GCA AAA TCT GTT GAC GAA CTG CTC    3168
Asn Thr Met Phe Thr Tyr Ser Lys Ala Lys Ser Val Asp Glu Leu Leu
            780             785             790

GGC AGC CAG GCG CTG TTG AAC GGT AAT GCC AAT GCT AAA AAA GCA GCA    3216
Gly Ser Gln Ala Leu Leu Asn Gly Asn Ala Asn Ala Lys Lys Ala Ala
            795             800             805

TCA CGG CGG ACG CGG CCT TGG TAT GTT ACG GAT GTT TCC GGA TAT TAC    3264
Ser Arg Arg Thr Arg Pro Trp Tyr Val Thr Asp Val Ser Gly Tyr Tyr
    810             815             820

AAT ATC AAG AAA CAC CTG ACC CTG CGC GCA GGT GTG TAC AAC CTC CTC    3312
Asn Ile Lys Lys His Leu Thr Leu Arg Ala Gly Val Tyr Asn Leu Leu
825             830             835             840

AAC TAC CGC TAT GTT ACT TGG GAA AAT GTG CGG CAA ACT GCC GGC GGC    3360
Asn Tyr Arg Tyr Val Thr Trp Glu Asn Val Arg Gln Thr Ala Gly Gly
            845             850             855

GCA GTC AAC CAA CAC AAA AAT GTC GGC GTT TAC AAC CGA TAT GCC GCC    3408
Ala Val Asn Gln His Lys Asn Val Gly Val Tyr Asn Arg Tyr Ala Ala
            860             865             870

CCC GGC CGA AAC TAC ACA TTT AGC TTG GAA ATG AAG TTT TAAACGTCCA    3457
Pro Gly Arg Asn Tyr Thr Phe Ser Leu Glu Met Lys Phe
            875             880             885

AACGCCGCAA ATGCCGTCTG AAAGGCTTCA GACGGCATTT TTTACACAAT            3507

TCCCACCGTT TCCCATCATC CCCGATACAC                                  3537
```

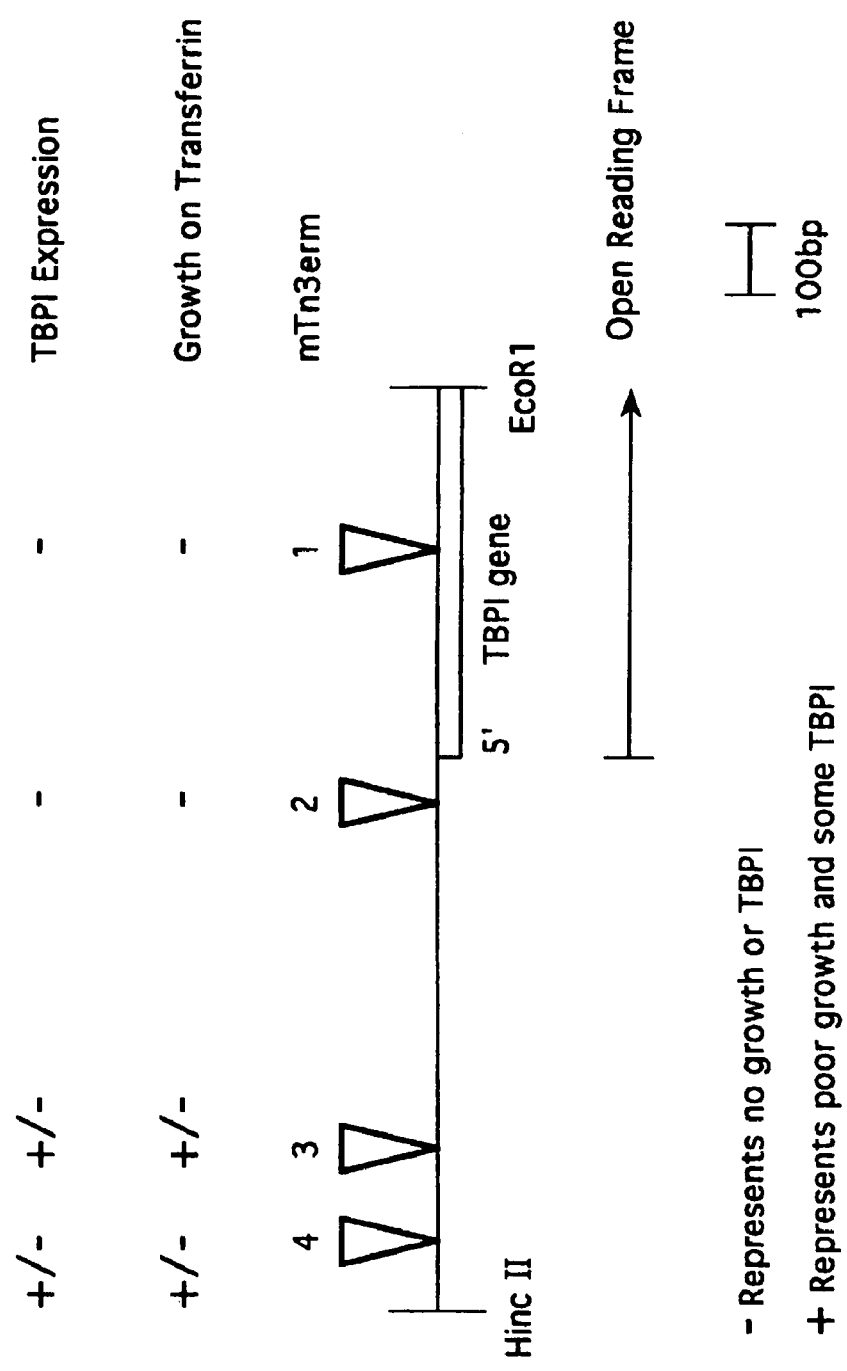

TRANSFERRIN-BINDING PROTEINS FROM *NEISSERIA GONORRHOEAE*

This application is a continuation of U.S. application Ser. No. 09/332,226, filed Jun. 14, 1999, now abandoned which is a continuation of U.S. application Ser. No. 08/363,124, filed Dec. 23, 1994, now U.S. Pat. No. 5,912,336, which is a continuation of U.S. application Ser. No. 08/124,254, filed Sep. 20,1993, now abandoned, which is a divisional application of U.S. application Ser. No. 07/973,336, filed Nov. 5, 1992, now abandoned, which is a continuation-in-part of number U.S. application Ser. No. 07/572,187, filed on Aug. 23, 1990, now abandoned, all of which are incorporated herein by reference.

The invention disclosed in the specification is directed to transferrin-binding proteins from *Neisseria gonorrhoeae* and *Neisseria meningitidis* as well as immunologically cross-reactive fragments and analogs thereof. The specification is further directed to antibodies raised against such proteins, as well as the use of such proteins and antibodies in the detection of *N. gonorrhoeae* and *N. meningitides* and treatment of diseases caused by *N. gonorrhoeae* and *N. meningitidis*. DNA encoding recombinant transferrin-binding proteins and cells that express such DNA are also covered by the present invention.

*N. gonorrhoeae* and *N. meningitidis* are two pathogens of the genus *Neisseria* that are genetically similar, but pathogenically different. Iron is an essential nutrient for the growth of *N. gonorrhoeae* and *N. meningitidis*, as it is for many bacteria. Unlike most other gram negative bacteria, *N. gonorrhoeae* and *N. meningitidis* do not produce and secrete small, soluble iron-chelating compounds, called siderophores. These other gram-negative bacteria have receptors capable of taking up the iron-siderophore complex.

Instead, *N. gonorrhoeae* and *N. meningitidis* are believed to possess membrane proteins that bind to the iron-binding glycoproteins lactoferrin and transferrin, which are present in human exocrine secretions and serum, respectively. *N. gonorrhoeae* and *N. meningitidis* are believed to take up iron in human hosts through the binding of lactoferrin and transferrin to these lactoferrin- and transferrin-binding membrane proteins, i.e, receptors.

The lactoferrin-binding protein from *N. meningitidis* is believed to be a 105 kD, iron-regulated outer membrane protein; see Schryvers and Morris, Infect. Immun. 56, 1144-1149 (1988). The transferrin-binding protein from one strain of *N. meningitidis* has been reported to be a 71 kD iron-regulated outer membrane protein, although other strains are reported to have transferrin-binding proteins with molecular weights of 75 kD-88 kD, 85 kD, and 95 kD; see Schryvers and Morris, Mol. Microbiol. 2, 281-288 (1988). These authors concede that the results of the various attempts at identifying the transferrin-binding protein of *N. meningitidis* are not consistent with each other. In fact, proteins of 85 kD and 95 kD are shown not to be necessary for transferrin receptor function in *N. meningitidis*; see Dyer et al., Microbial Pathogenesis 3, 351-363 (1987).

The ability of *N. gonorrhoeae* to assimilate iron has also been of interest. In one investigation, a dot binding assay involving the use of gonococcal total membranes derived from cells grown under iron-deficient conditions suggested the presence of separate receptors for lactoferrin and transferrin. The molecular weight and other properties of the binding proteins are not determined. See Lee and Schryvers, Mol. Microbiol. 2, 827-829 (1988). Therefore, the identity of the binding proteins in *N. gonorrhoeae* has not previously been established.

The diseases caused by gonococcal and meningococcal infection are pervasive and often serious. Improved methods for preventing, detecting and treating such diseases, such as gonorrhea, meningitis and septic shock are needed.

The growth of *N. gonorrhoeae* and *N. meningitidis* in humans can be inhibited by reducing the ability of these cells to take up iron. A reduction in the ability of gonococcal and meningococcal cells to assimilate iron in the bloodstream could be accomplished by blocking the transferrin receptor function. The transferrin receptor, for example, could be blocked by antibodies against the receptor. In order to raise antibodies against the receptor, however, the receptor must be identified so that it can be isolated.

There is, therefore, a need for identifying, isolating and purifying the transferrin-binding proteins from *N. gonorrhoeae* and *N. meningitidis*. DNA molecules encoding such proteins are needed in order to produce recombinant transferrin binding proteins. Antibodies against the transferrin binding proteins are needed in order to inhibit transferrin receptor function. Vaccines are needed to prevent and to treat gonococcal and meningococcal infections. Antibody and nucleic acid probes are needed to detect *N. gonorrhoeae* and *N. meningitidis*. It is the object of the present invention to provide such proteins, antibodies, DNA molecules and vaccines for detecting, preventing and treating gonococcal and meningococcal infections.

SUMMARY OF THE INVENTION

These and other objectives as will become apparent to those having ordinary skill in the art have been achieved by providing an iron-regulated protein found in *Neisseria gonorrhoeae* or *Neisseria meningitidis* outer membranes,
wherein the protein is substantially free of:
 (a) detergent;
 (b) nitrocellulose/cellulose acetate paper; and
 (c) other iron-regulated proteins from *Neisseria gonorrhoeae* and *Neisseria meningitidis*;
wherein the protein is isolatable by means of a transferrin affinity column;
wherein the protein binds specifically to antisera raised against an iron-regulated outer membrane protein having a molecular weight of approximately 100 kD found in *Neisseria gonorrhoeae*; and
wherein the protein is important in transferrin receptor function in *Neisseria gonorrhoeae* or *Neisseria meningitidis*; and functional analogs of such proteins.

The invention further provides DNA molecules that express the transferrin binding protein and its analogs in a host cell. The resulting recombinant protein is also part of the invention.

The invention also includes antibodies against the transferrin-binding proteins of the invention. The antibodies inhibit growth of *N. gonorrhoeae* and/or *N. meningitidis*, and are useful in controlling infections of these pathogens.

The invention further includes vaccine compositions comprising the transferrin-binding proteins of the invention and analogs of such proteins, as well as methods of immunizing a host against gonococcal and meningococcal diseases, such as gonorrhea, meningitis, and septic shock, by administering such vaccines. The antibodies of the invention may be used in passive immunization to treat gonococcal and meningococcal diseases.

DESCRIPTION OF THE FIGURES

FIG. 1 shows the entire DNA and amino acid sequence encoding the 100 kD gonoccocal transferrin binding protein 1

(TBP1). The start codon encoding the first amino acid of the mature protein occurs at nucleotide 406. The stop codon for the protein occurs at nucleotide 3153. See example 6a and example 7. See SEQ ID NO:1 and SEQ ID NO:2.

Figure 2:
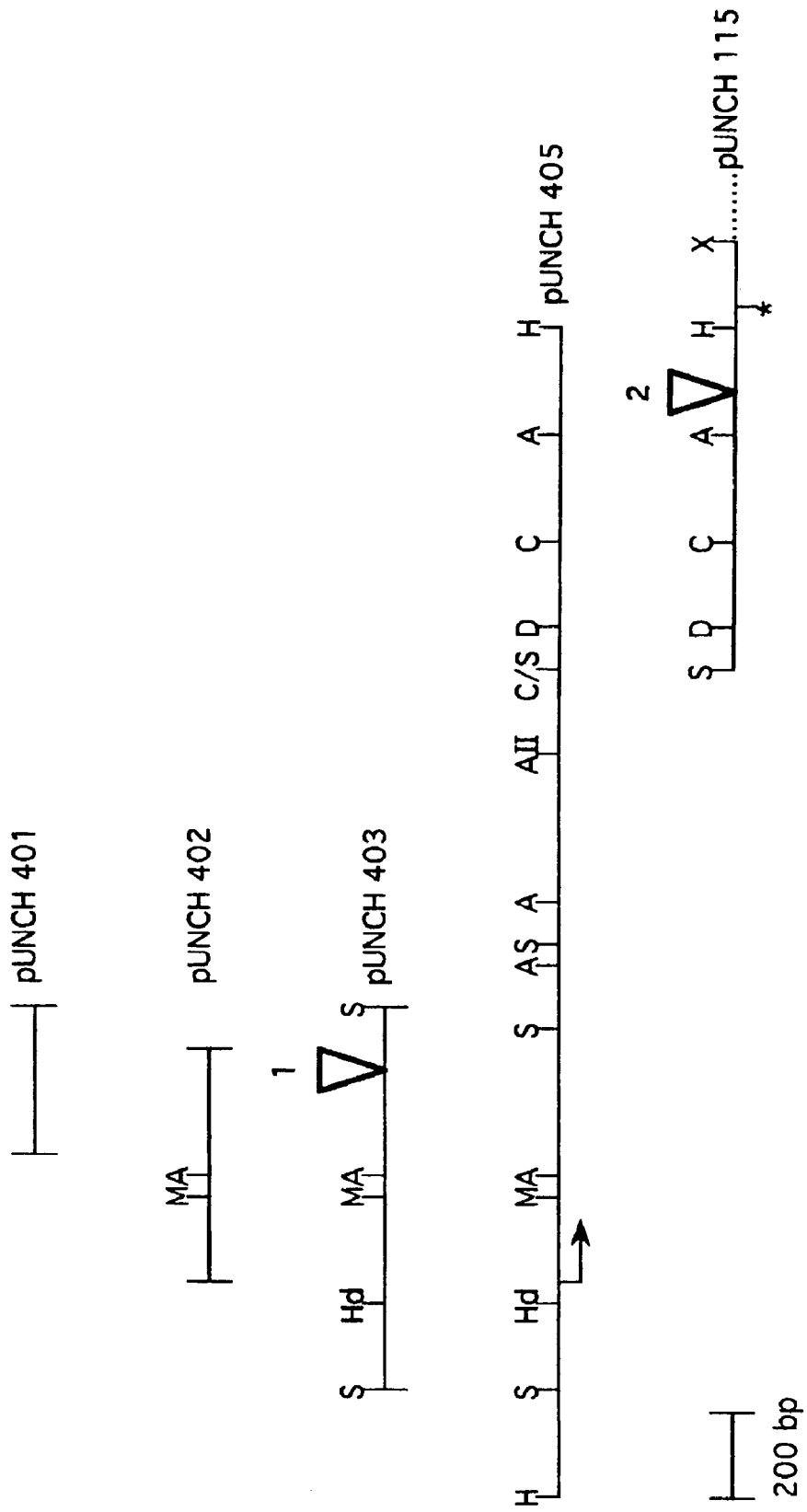

FIG. 2 represents transferrin binding protein 1 clones from which the entire gene sequence for the protein is derived.

Figure 3:
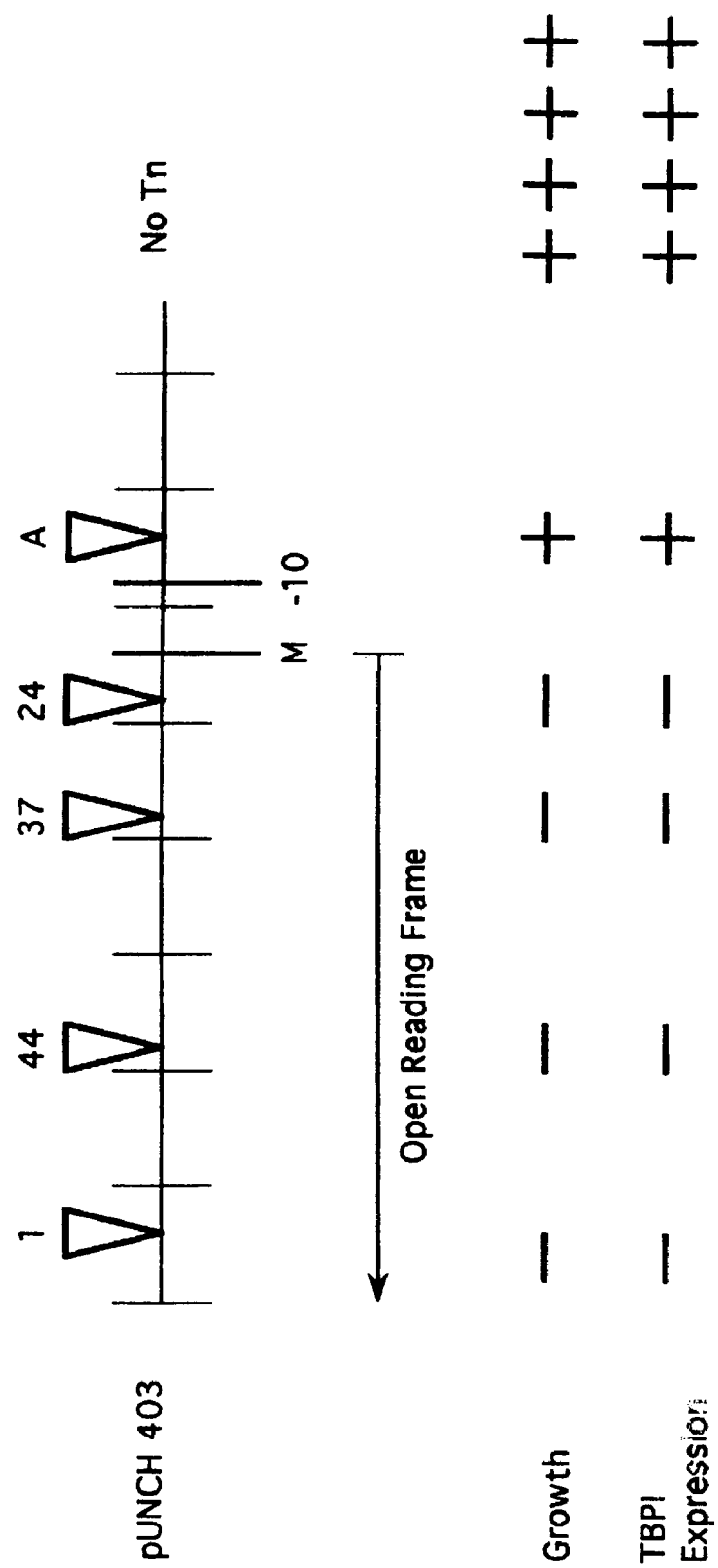

FIG. 3 shows positions of transposon insertions within the 100 kD gonococcal transferrin binding protein fragment in pUNCH403 and corresponding phenotypes of respective mutants. Transposons (mTn3CAT) are inserted by shuttle mutagenesis in *E. coli*. Chloramphenicol resistant transformants are selected in FA19 to create mutants. Below each transposon insertion (indicated by inverted triangle), growth on 2.5 µM human transferrin (25% saturated with Fe) and expression of protein as assayed by Western blot are indicated by + or –. The open reading frame, indicated by an arrow, reads right to left and begins with methionine, designated M. A typical –10 sequence was found (–10) but no canonical –35 sequence could be identified. Wild-type growth and protein expression are shown at right under the heading "No Tn". See example 9.

FIG. 4 shows a strategy for cloning the meningococcal 95 kD transferrin binding protein gene. The figure is not drawn to scale. The 1.3 kb HincII/EcoRI fragment shown in step 1 is cloned from a lambda Zap II library using the anti-100 kD protein antibody probe described in Example 4. The method for screening the library is described in Example 6a. The 5.0 kb fragment shown in step 2 is cloned from a partial ClaI library in pHSS6-GCU using the 1.3 kb fragment as a probe. The 2.0 kb EcoRI/HincII fragment in step 3 is cloned from a lambda Zap II library using the 1.7 kb EcoRI/ClaI restriction fragment from step 2 as a probe. The 2.5 kb EcoRI/HincII fragment shown in step 4 is cloned from a lambda Zap II library using the 2.0 kb EcoRI/HincII fragment from step 3. The fragments from steps 1-4 fit together as shown in the fragment entitled "FAM20 Chromosome". See example 10.

FIG. 5 shows the entire DNA and amino acid sequence of the 95 kd meningococcal transferrin-binding protein. The ATG start codon encoding the first amino acid of the mature protein occurs at nucleotide 721. The stop codon is at nucleotide 3450. See example 10. See SEQ ID NO:3 and SEQ ID NO:4.

FIG. 6 shows the results of transposon mutagenesis experiments involving the 1.3 kb HincII/EcoRI fragment from step 1 of FIG. 4. See example 11.

DETAILED DESCRIPTION OF THE INVENTION

Isolation of Proteins from Bacteria

Transferrin-binding proteins are prepared from the membranes of *N. gonorrhoeae* or *N. meningitidis*. The membranes may be prepared by methods known in the art. The method described by Schryvers and Morris in Infect. Immun. 56, 1144-1149 (1988) is suitable. This method is incorporated herein by reference.

The membranes are obtained from cells grown in an iron-deficient medium. The growth medium may be a standard growth medium such as GC medium base (gonococcal medium base) supplied by Difco. This medium can be made iron-deficient by the addition of chelating agents such as ethylenediaminetetraacetic acid (EDTA), ethylene-diamine-di-ortho-hydroxyphenylacetic acid (EDDA), or desferal (Ciba Pharmaceuticals). Alternatively, the growth medium may be a mechanically defined medium described by Mickelsen and Sparling (Inf. Immun. 33, 555-564 (1981)), which is made iron-deficient by treatment with the chelating agent Chelex-100 (Bio-Rad).

Any gonococcal and meningococcal strains that have normal transferrin receptor function are useful in the present invention. Such strains are generally available from clinical and other sources, such as the American Type Culture Collection, Bethesda, Md. and the Neisseria Repository, NAMRU, University of California, Berkley.

For example, gonococcal strains FA19, which is described in McKenna et al, Infect. Immun. 56, 785-791 (1988); FA248, which is described in Biswas et al, J. Bacteriol. 151, 77-82 (1979); and F62, which is described in West and Sparling, Infect. and Immun. 47, 388-394 (1985) constitute suitable sources of the gonococcal transferrin protein. Meningococcal strains FAM18 and FAM20 (Dyer et al., Microbial Pathogenesis 3, 351-363 (1987)) and B16B6, group X and group W135 (Schryvers and Morris 56, 1144-1149 (1988)) are representative of sources of the meningococcal transferrin binding protein.

Proteins that bind to transferrin may be isolated from other membrane proteins of iron-starved *N. gonorrhoeae* and *N. meningitidis* with immobilized transferrin using affinity procedures known in the art; see, for example, Schryvers and Morris, Infect. Immun. 56, 1144-1149 (1988). The method of Schryvers and Morris is incorporated herein by reference. A variation of this procedure, which is described in Example 2a, is preferably used to resolve the transferrin binding proteins from gonococcal and meningococcal, membrane proteins.

Briefly, membranes from iron-starved gonococcal and meningococcal cells are isolated and treated with biotinylated transferrin. The resulting complex is immobilized by, for example, treating the complex with avidin- or streptavidin-agarose. The affinity resin pellet is thoroughly washed and suspended in buffer. The transferrin receptor is separated from the immobilized transferrin by, for example, heating. The proteins are separated by, for example, SDS-PAGE in accordance with the method of Laemmli, Nature 227, 680-685 (1970). A protein having a molecular weight of approximately 100 kD, hereinafter 100 kD protein, is resolved from gonococci. A protein having a molecular weight of approximately 95 kD, hereinafter, 95 kD protein, is resolved from meningococci.

Identification of Proteins

The molecular weights are determined by resolving single bands on SDS-PAGE and comparing their positions to those of known standards. The method is understood by those in the art to be accurate within a range of 3-5%. The molecular weights varied slightly between determinations. The molecular weight of the protein from gonococci is consistently and repeatably higher than that from meningococci, and varied from 97-100 kD.

Confirmation that the 100 kD transferrin-binding protein from *N. gonorrhoeae* is important for transferrin receptor function is obtained by preparing five different gonococcal mutants deficient in transferrin receptor activity. Each mutant is tested for the presence of the 100 kD transferrin-binding protein by western blot using polyclonal antisera raised in rabbits. In each mutant, the amount of 100 kD outer membrane protein is much less than is observed for wild-type gonococcal strains. Other mutant gonococcal strains that have normal transferrin receptor activity had wild-type levels of the 100 kD protein in their membranes.

A similar experiment establishes that the 95 kD protein from meningococci is important for transferrin receptor function. The western blot analysis is performed with antisera raised against the 100 kD protein from *N. gonorrhoeae*, which is found to cross-react with the 95 kD protein from *N. meningitidis*. Thus, in both *N. gonorrhoeae* and *N. meningiti-*

*dis*, the lack of transferrin receptor activity correlates with the absence of the 100 kD and 95 kD proteins, respectively.

Therefore, contrary to expectations based on the prior art, the iron-regulated 100 kD outer membrane protein found in *N. gonorrhoeae* is the transferrin receptor. The iron-regulated 95 kD outer membrane protein found in *N. meningitidis* surprisingly cross-reacts with antisera raised against the 100 kD protein found in *N. gonorrhoeae*, and is the *N. meningitidis* transferrin receptor. Antisera raised in mammals, such as rabbits, mice, goats, monkeys and humans, against the transferrin receptor from *N. gonorrhoeae* are generally cross-reactive with the transferrin receptor from *N. meningitidis* and vice versa. Monoclonal antibodies are also generally cross-reactive with the 95 kD and 100 kD proteins.

As used herein, transferrin receptor from *N. gonorrhoeae* and *N. meningitidis* include the iron-regulated 100 kD outer membrane protein from *N. gonorrhoeae* and the iron-regulated 95 kD outer membrane protein from *N. meningitidis*. It should be understood that these transferrin receptors constitute a class of proteins. The class includes, for example, variations in the amino acid sequence that occur naturally in the various strains of *N. gonorrhoeae* and *N. meningitidis*.

The proteins of the present invention further include functional analogs of the 100 kD or the 95 kD transferrin receptors from *N. gonorrhoeae* or *N. meningitidis*, respectively. A protein is considered a functional analog of another protein for a specific function, as described below, if the analog is immunologically cross-reactive with, and has the same function as, the other protein. The analog may, for example, be a fragment of the protein, or a substitution, addition or deletion mutant of the protein.

The proteins and functional analogs of the present invention are essentially pure. For the purposes of this specification, essentially pure means that the proteins and functional analogs are free from all but trace amounts of other iron-regulated proteins from *N. gonorrhoeae* and *N. meningitidis* as well as of materials used during the purification process. The other iron-regulated proteins from *N. gonorrhoeae* and *N. meningitidis* include other transferrin binding proteins. Materials used in the purification process include detergents, affinity binding agents and separation films. Detergents include sodium dodecyl sulfate and sarcosine. Affinity binding agents include agarose, avidin-agarose, streptavidin-agarose, biotin and biotinylated proteins, such as biotinylated transferrin. Separation films include nitrocellulose paper and nitrocellulose/cellulose acetate paper.

Recombinant DNA

Methods are known for isolating DNA once the protein has been isolated and purified. Many of these methods are described in Maniatis et al, "Molecular Cloning: A Laboratory Manual," Cold Spring Harbor Laboratory Press (1982). The immunological screening method is preferred.

For example, chromosomal DNA from a gonococcal or meningococcal strain capable of utilizing iron bound to transferrin, such as those described above, is isolated and cleaved into fragments of suitable size by standard methods. Suitable DNA cleavage methods include, for example, sonication and the use of restriction endonucleases. A suitable average fragment size is approximately 0.5-10 kbp.

Linkers are added to the fragments and the resulting fragments are ligated into a suitable vector. The linker corresponds to a restriction site in the vector. Suitable linkers include, for example, EcoRI, PstI and BamHI. A suitable vector is lambda-gt11. Ligated DNA may be packaged by commercial kits, such as a kit manufactured by Promega.

Proteins from the resulting library are cloned and expressed in a suitable host, typically *E. coli*. Cloning is preferably performed in an *E. coli* host carrying the following mutations: mcrA, mcrB, mcrC, mrr, hsdS, hsdR, and hsdM. Some suitable *E. coli* strains include DH5alphaMCR (BRL) and "SURE" (Stratagene).

The plaques that are obtained are screened immunologically by methods known in the art. Maniatis, Id. A suitable method is described in Example 6 below. Screening may be facilitated by the use of a commercial screening kit, such as the Picoblue Immunological Screening Kit of Stratagene (La Jolla, Calif.) in accordance with the accompanying Stratagene protocol, which is available from Stratagene or from the file history of this specification.

Plaques that bind the transferrin-binding protein specific antisera are selected from non-reacting plaques and purified. Maniatis, Id. The DNA from purified phage is isolated by methods known in the art. Suitable methods include, for example, polyethylene glycol precipitation, phage lysis, and anion exchange chromatography, which can be facilitated by the use of a kit manufactured by Qiagen (Studio City, Calif.).

The DNA obtained may be amplified by methods known in the art. One suitable method is the polymerase chain reaction (PCR) method described by Mullis et al in U.S. Pat. No. 4,683,195 and by Sambrook, Fritch and Maniatis (eds) in Molecular Cloning, A Laboratory Manual, Second Edition, Cold Spring Harbor Laboratory Press (1989). It is convenient to amplify the DNA clones in the lambda-gt11 vectors using lambda-gt11-specific oligomers available from New England Biolabs.

Amplified clones are inserted into suitable vectors and sequenced in accordance with methods known in the art. A suitable sequencing method is the dideoxy chain terminating method described by Sanger et al. in Proc. Natl. Acad. Sci. USA 74, 5463-5467 (1977).

Suitable vectors and polymerases for sequencing are known. A suitable vector is the Bluescript vector of Stratagene. A suitable polymerase is Sequenase (United States Biochemical Corp., Cleveland, Ohio).

In the immunoscreening method described above, it is usually necessary to screen a large number of plaques in order to identify fragments with the transferrin-binding protein specific antisera. For example, in one experiment, approximately 500,000 plaques are obtained from fragments of a gonococcal (FA19) chromosome. Two plaques are identified using the antisera against the 100 kD transferrin-binding protein from *N. gonorrhoeae*. A clone having an insert size of 323 bp (pUNCH401) is isolated from one plaque, while a clone with an insert size of 483 bp (pUNCH402) is isolated from the other plaque. These DNA sequences represent overlapping fragments of the FA19 chromosome. The consensus sequence of the two fragments, including the overlap, is shown as FIG. 1. Nucleotides 75 to 323 represent the overlapping sequences. Nucleotides 1 to 74 represent the non-overlapping sequence of the 323 bp fragment. Nucleotides 324 to 558 represent the non-overlapping sequence of the 483 bp fragment. The only open reading frame runs in the direction opposite to that shown in FIG. 1 (i.e. from nucleotide 558 to nucleotide 1). See example 6a.

The fragments described above, or sub-fragments of them, can be used as probes for obtaining additional fragments of the transferrin-binding protein gene. Using this technique, an 8 kb ClaI fragment and a 3.2 kb HincII fragment in the FA19 chromosome hybridizes to the 323 and 483 bp fragments. A restriction map of the 3.2 kb HincII fragment is shown in FIG. 2. Fragments obtained can be sequenced. See examples 7 and 8.

By suitable extensions of the fragments, the entire gene is sequenced. The limits of the coding sequence are determined by methods known in the art, such as by insertional mutagenesis. See example 9. Similar methods are used to determine the sequence of the 95 kD meningococcal transferrin binding protein. See examples 10 and 11 and FIGS. 4-6.

Recombinant Proteins

The proteins of the present invention may be produced by means of recombinant DNA technology. Suitable methods for producing recombinant proteins from isolated DNA are described in Maniatis et al., Id.

Briefly, DNA coding for the transferrin-binding proteins of the present invention, as well as DNA coding for their functional analogs, may be expressed using a wide variety of host cells and a wide variety of vectors. The host may be prokaryotic or eukaryotic. The DNA may be obtained from natural sources and, optionally, modified. The DNA may also be synthesized in whole or in part.

The vector may comprise segments of chromosomal, non-chromosomal and synthetic DNA sequences. Some suitable prokaryotic vectors include plasmids from *E. coli* such as colE1, pCR1, pBR322, pMB9, and RP4. Prokaryotic vectors also include derivatives of phage DNA such as M13 and other filamentous single-stranded DNA phages.

Vectors useful in yeast are available. A suitable example is the 2μ plasmid.

Suitable vectors for use in mammalian cells are also known. Such vectors include well-known derivatives of SV-40 adenovirus, retrovirus-derived DNA sequences and vectors derived from combination of plasmids and phage DNA.

Further eukaryotic expression vectors are known in the art (e.g., P. J. Southern and P. Berg, J. Mol. Appl. Genet. 1, 327-341 (1982); S. Subramani et al, Mol. Cell. Biol. 1, 854-864 (1981); R. J. Kaufmann and P. A. Sharp, "Amplification And Expression Of Sequences Cotransfected with A Modular Dihydrofolate Reductase Complementary DNA Gene," J. Mol. Biol. 159, 601-621 (1982); R. J. Kaufmann and P. A. Sharp, Mol. Cell. Biol. 159, 601-664 (1982); S. I. Scahill et al, "Expression And Characterization Of The Product Of A Human Immune Interferon DNA Gene In Chinese Hamster Ovary Cells," Proc. Natl. Acad. Sci. USA 80, 4654-4659 (1983); G. Urlaub and L. A. Chasin, Proc. Natl. Acad. Sci. USA 77, 4216-4220, (1980).

Useful expression hosts include well-known prokaryotic and eukaryotic hosts. Some suitable prokaryotic hosts include, for example, *E. coli*, such as *E. coli* SG-936, *E. coli* HB 101, *E. coli* W3110, *E. coli* X1776, *E. coli* X2282, *E. coli* DHI, and *E. coli* MRC1, *Pseudomonas, Bacillus*, such as *Bacillus subtilis*, and *Streptomyces*. Suitable eukaryotic cells include yeasts and other fungi, insect, animal cells, such as COS cells and CHO cells, human cells and plant cells in tissue culture.

The expression vectors useful in the present invention contain at least one expression control sequence that is operatively linked to the transferrin-binding protein gene or fragment thereof. The control sequence is inserted in the vector in order to control and to regulate the expression of the cloned DNA sequence. Examples of useful expression control sequences are the lac system, the trp system, the tac system, the trc system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast alpha-mating factors, and promoters derived from polyoma, adenovirus, retrovirus, and simian virus, e.g., the early and late promoters or SV40, and other sequences known to control the expression of genes of prokaryotic or eukaryotic cells and their viruses or combinations thereof.

The 100 kD or 95 kD proteins may be purified by methods known in the art. For example, the entire transferrin binding proteins or portions thereof may be expressed in the form of a fusion protein with an appropriate fusion partner. The fusion partner preferably facilitates purification and identification. Some useful fusion partners include beta-galactosidase (Gray, et al., Proc. Natl. Acad. Sci. USA 79, 6598 (1982)); trpE (Itakura et al., Science 198, 1056 (1977)) and protein A (Uhlen et al., Gene 23 369 (1983)). For example, fusion proteins containing beta-galactosidase may be purified by affinity chromatography using an anti-beta-galactosidase antibody column (Ullman, Gene. 29, 27-31 (1984)).

It is preferable that the DNA that encodes the fusion protein is engineered so that the fusion protein contains a cleavable site between the transferrin binding protein and the fusion partner. Both chemical and enzymatic cleavable sites are known in the art. Suitable examples of sites that are cleavable enzymatically include sites that are specifically recognized and cleaved by collagenase (Keil et al., FEBS Letters 56, 292-296 (1975)); enterokinase (Hopp et al., Biotechnology 6, 1204-1210 (1988)); factor Xa (Nagai et al., Methods Enzymol. 153, 461-481 (1987)); thrombin (Eaton et al., Biochemistry 25, 505 (1986)); and glutathione S-transferase (Johnson, Nature 338, 585 (1989); and Van Etten et al., Cell 58, 669 (1989)). Collagenase cleaves between proline and X in the sequence Pro-X-Gly-Pro wherein X is a neutral amino acid. Enterokinase cleaves after lysine in the sequence Asp-Asp-Asp-Asp-Lys (SEQ. ID NO:5) Factor Xa cleaves after arginine in the sequence Ile-Glu-Gly-Arg(SEQ ID NO:6). Thrombin cleaves between arginine and glycine in the sequence Arg-Gly-Ser-Pro (SEQ ID NO:7).

Specific chemical cleavage agents are also known. For example, cyanogen bromide cleaves at methionine residues in proteins.

Alternatively, the 100 kD and 95 kD transferrin receptor proteins may be overexpressed behind an inducible promoter and purified by affinity chromatography using specific transferrin receptor antibodies. As another alternative, the overexpressed protein may be purified using a combination of ion-exchange, size-exclusion, and hydrophobic interaction chromatography using methods known in the art. These and other suitable methods are described by Marston, "The Purification of Eukaryotic Polypeptides Expressed in *E. coli*" in *DNA Cloning*, D. M. Glover, Ed., Volume III, IRL Press Ltd., England, 1987.

UTILITY

Proteins as Probes

The 100 kD protein from *N. gonorrhoeae*, the 95 kD protein from *N. meningitidis*, and their functional analogs are useful in detecting and preventing diseases caused by gonococcal and meningococcal infection.

For example, the proteins may be labelled and used as probes in standard immunoassays to detect antibodies against the proteins in samples, such as in the sera or other bodily fluids of patients being tested for gonorrhea, septic shock, or meningitis. In general, a protein in accordance with claim A or a functional derivative of such a protein is incubated with the sample suspected of containing antibodies to the protein. The protein is labelled either before, during, or after incubation. The detection of labelled protein bound to an antibody in the sample indicates the presence of the antibody. The antibody is preferably immobilized.

Suitable assays for detecting antibodies with proteins are known in the art, such as the standard ELISA protocol described by R. H. Kenneth, "Enzyme-Linked Antibody Assay with Cells Attached to Polyvinyl Chloride Plates" in Kenneth et al, *Monoclonal Antibodies*, Plenum Press, N.Y., page 376 (1981). Briefly, plates are coated with a sufficient amount of an antigenic protein to bind detectable amounts of the antibody. After incubating the plates with the polypeptide, the plates are blocked with a suitable blocking agent, such as, for example, 10% normal goat serum. The sample, such as patient sera, is added and titered to determine the endpoint. Positive and negative controls are added simultaneously to quantitate the amount of relevant antibody present in the unknown samples. Following incubation, the samples are probed with goat anti-human Ig conjugated to a suitable enzyme. The presence of anti-protein antibodies in the sample is indicated by the presence of the enzyme.

For use in immunoassays, the protein may be labelled with radioactive or non-radioactive atoms and molecules. Such labels and methods for conjugating them to proteins are known in the art.

Some examples of useful radioactive labels include $^{32}$P, $^{125}$I, $^{131}$I, and $^3$H. Use of radioactive labels have been described in U.K. 2,034,323, U.S. Pat. No. 4,358,535, and U.S. Pat. No. 4,302,204.

Some examples of non-radioactive labels include enzymes, chromophors, atoms and molecules detectable by electron microscopy, and metal ions detectable by their magnetic properties.

Some useful enzymatic labels include enzymes that cause a detectable change in a substrate. Some useful enzymes and their substrates include, for example, horseradish peroxidase (pyrogallol and o-phenylene-diamine), beta-galactosidase (fluorescein beta-D-galactopyranoside), and alkaline phosphatase (5-bromo-4-chloro-3-indolyl phosphate/nitro blue tetrazolium). The use of enzymatic labels have been described in U.K. 2,019,404, EP 63,879, and by Rotman, Proc. Natl. Acad. Sci., 47, 1981-1991 (1961).

Useful chromophores include, for example, fluorescent, chemiluminescent, and bioluminescent molecules, as well as dyes. Some specific chromophores useful in the present invention include, for example, fluorescein, rhodamine, Texas red, phycoerythrin, umbelliferone, luminol.

The labels may be conjugated to the probe by methods that are well known in the art. The labels may be directly attached through a functional group on the probe. The probe either contains or can be caused to contain such a functional group. Some examples of suitable functional groups include, for example, amino, carboxyl, sulfhydryl, maleimide, isocyanate, isothiocyanate.

The label may also be conjugated to the probe by means of a ligand attached to the probe by a method described above and a receptor for that ligand attached to the label. Any of the known ligand-receptor combinations is suitable. The biotin-avidin combination is preferred.

For use in immunoassays, the proteins may be the entire 100 kD or 95 kD protein or may be functional analogs thereof. Functional analogs of these proteins include fragments and substitution, addition and deletion mutations that do not destroy the ability of the proteins to bind to their antibodies. As long as the proteins are able to detect antibodies specific for the transferrin-binding proteins, they are useful in the present invention.

Proteins in Vaccines

Since the transferrin-binding proteins of the present invention are important for a vital function of *N. gonorrhoeae* and *N. meningitidis*, and are found on the outer membranes, these proteins are useful in vaccines for the prevention of diseases caused by *Neisseria* infections, such as gonorrhea, septic shock, and meningitis. For this purpose, it is necessary for the protein to produce neutralizing antibodies. Neutralizing antibodies are antibodies that significantly inhibit the growth of and/or kill the bacterial cells in vitro or in vivo. Growth of the bacteria is significantly inhibited in vivo if the inhibition is sufficient to prevent or reduce the symptoms of the disease of a mammal infected with the disease.

Vaccines comprising the 100 kD or 95 kD protein or functional analogs as antigen may be used to inhibit the growth of, or kill, the gonococci or meningococci in accordance with the invention. Functional analogs of the 100 kD and 95 kD proteins for this purpose include fragments and substitution, addition or deletion mutations that produce neutralizing antibodies in a mammalian host such as in a human host.

The present invention further includes vaccine compositions for immunizing mammals, including humans, against infection by *N. gonorrhoeae* and *N. meningitidis*. The vaccines comprise the 100 kD transferrin receptor from *N. gonorrhoeae* and/or the 95 kD transferrin receptor from *N. meningitidis* and pharmaceutically acceptable adjuvants. Instead of the 100 kD and 95 kD proteins, functional analogs may be substituted, as described above.

The vaccine comprises the antigen in a suitable carrier. The vaccine may include adjuvants, such as muramyl peptides, and lymphokines, such as interferon, interleukin-1 and interleukin-6. The antigen may be adsorbed on suitable particles, such as aluminum oxide particles, or encapsulated in liposomes, as is known in the art.

The antigen may also be delivered in an avirulent strain of *Salmonella*, such as *S. typhimurium*. Such vaccines may be prepared by cloning DNA comprising the active portion of the transferrin binding protein in the *Salmonella* strain, as is known in the art; see, for example, Curtiss et al., Vaccine 6, 155-160 (1988) and Galan et al., Gene 94, 29-35 (1990).

The invention further includes methods of immunizing host mammals, including humans, with the vaccine compositions described above. The vaccine may be administered to a mammal by methods known in the art. Such methods include, for example, intravenous, intraperitoneal, subcutaneous, or intramuscular administration.

The vaccine composition may contain the entire 100 kD protein or the 95 kD protein, but preferably contains a non-toxic fragment of the 100 kD or 95 kD protein. It is well known, for example, to produce fragments of antigenic proteins and to determine those fragments that contain the antigenic site. The length of the fragment is not critical as long as the fragment is antigenic and non-toxic. Therefore, the fragment should contain sufficient amino acid residues to define the epitope. Methods for isolating and identifying antigenic fragments from known antigenic polypeptides are described by Salfeld et al. in J. Virol. 63, 798-808 (1989) and by Isola et al. in J. Virol. 63, 2325-2334 (1989).

If the fragment defines the epitope, but is too short to be antigenic, it may be conjugated to a carrier molecule. Some suitable carrier molecules include keyhole limpet hemocyanin and bovine serum albumen. Conjugation may be carried out by methods known in the art. One such method is to combine a cysteine residue of the fragment with a cysteine residue on the carrier molecule.

Antibodies for Treatment

Further, the invention includes isolating neutralizing antibodies that specifically recognize and bind to the proteins and functional analogs of the invention. The antibodies may be polyclonal or monoclonal. The definitions of neutralizing antibodies and functional analogs used in conjunction with vaccines (see above) apply as well to the production of neutralizing antibodies Polyclonal antibodies are isolated from mammals that have been innoculated with the protein or a functional analog in accordance with methods known in the art. The monoclonal antibodies may be produced by methods known in the art. These methods include the immunological method of Kohler and Milstein, Nature 256, 495-497 (1975) and the recombinant DNA method described by Buse et al. in Science 246, 1275-1281 (1989).

The invention also includes methods of treating mammals, including humans, suffering from diseases caused by *N. gonorrhoeae* or *N. meningitidis* by administering to such mammals an effective amount of the neutralizing antibodies of the invention. Administration may be by the same methods described above for administering vaccines.

Antibodies as Probes

The transferrin-binding proteins and functional analogs of the invention may also be used to produce antibodies for use as probes to detect the presence of *Neisseria* gonorhoeae or *Neisseria meningitidis* in a sample. The antibodies may be polyclonal or monoclonal. For this purpose, functional analogs include fragments and substitution, addition and deletion mutations of the 100 kD protein or of the 95 kD protein as long as the analogs also produce antibodies capable of detecting the presence of the 100 kD or 95 kD proteins in a sample. The sample may, for example, be a bodily fluid from a mammal, including a human, suspected of being infected with *N. gonorrhoeae* or *N. meningitidis*.

Assays for detecting the presence of proteins with antibodies have been previously described, and follow known formats, such as standard blot and ELISA formats. These formats are normally based on incubating an antibody to a sample suspected of containing the 95 kD or 100 kD protein and detecting the presence of a complex between the antibody and the protein. The antibody is labelled either before, during, or after the incubation step. The protein is preferably immobilized prior to detection. Immobilization may be accomplished by directly binding the protein to a solid surface, such as a microtiter well, or by binding the protein to immobilized antibodies.

When used as probes, the antibodies are normally labelled by methods known in the art. The same labels useful for proteins (see above) are also useful for antibodies. Methods for labelling antibodies have been described, for example, by Hunter and Greenwood in Nature 144, 945 (1962) and by David et al. in Biochemistry 13, 1014-1021 (1974). Additional methods for labelling antibodies have been described in U.S. Pat. Nos. 3,940,475 and 3,645,090.

Nucleic Acid Molecules as Probes

Nucleic acid molecules encoding the 100 kD protein, the 95 kD protein, or fragments of the 100 kD or 95 kD proteins having unique sequences may be used to detect the presence of *N. gonorrhoeae* or *N. meningitidis*. The nucleic acid molecules may be RNA or DNA.

Methods for determining whether a nucleic acid molecule probe recognizes a specific nucleic acid molecule in a sample are known in the art. Generally, a labelled probe that is complementary to a nucleic acid sequence suspected of being in a sample is prepared. Preferably, the target nucleic acid molecule is immobilized. The presence of probe hybridized to the target nucleic acid molecule indicates the presence of the nucleic acid molecule in the sample. Examples of suitable methods are described by Dallas et al. in "The Characterization of an *Escherichia Coli* Plasmid Determinant that Encodes for the Production of a Heat-labile Enterotoxin." in K. N. Timmis and A. Puehler, eds, *Plasmids of Medical, Environmental, and Commercial Importance*, Elsevier/North-Holland Publishing Co., Amsterdam, pages 113-122 (1975); Grunstein and Hogness in Proc. Natl. Acad. Sci USA 72, 3961-3965 (1975); Palva et al. in U.S. Pat. No. 4,731,325, which is assigned to Orion-yhtyma, Espoo, Finland; Mullis et al. in U.S. Pat. No. 4,683,195, which is assigned to Cetus Corporation, Emeryville, California; Schneider et al. in U.S. Pat. No. 4,882,269, which is assigned to Princeton University, and Segev in PCT Application WO 90/01069. The Schneider et al. patent and the Segev application are both licensed to ImClone Systems Inc., New York City.

The probes described above are labelled in accordance with methods known in the art. Methods for labelling oligonucleotide probes have been described, for example, by Leary et al, Proc. Natl. Acad. Sci. USA (1983) 80:4045; Renz and Kurz, Nucl. Acids Res. (1984) 12:3435; Richardson and Gumport, Nucl. Acids Res. (1983) 11:6167; Smith et al, Nucl. Acids Res. (1985) 13:2399; and Meinkoth and Wahl, Anal. Biochem. (1984) 138:267.

EXAMPLES

1. Bacterial Strains and Culture Conditions

Gonococcal strain FA19 is passed from frozen stock once on GCB agar and then used to inoculate flasks containing 1 liter of GCB broth to a starting density of 20 KU (Klett units). The culture is grown with 5% $CO_2$ at 37° C. with vigorous shaking until reaching a density of 40 KU at which time the chelator, desferal, is added to a final concentration of 50 μM. Cells are harvested 4 hours after addition.

Meningococcal strain FAM20 is prepared is the same manner as gonococcal strain FA19, except for the use of Chelex-treated CDM instead of GCB and desferal.

2a. Affinity Purification of Gonococcal Transferrin-binding Protein

The methods used for the preparation of membranes and isolation and purification of the gonococcal transferrin-binding protein is similar to that of Schryvers and Morris Infect. and Immun. 56, 1144-1149 (1988) for the preparation of meningococcal lactoferrin-binding protein. This method in the paper of Schryvers and Morris is incorporated herein by reference. The following modifications of the method of Schryvers and Morris are introduced. 625 μg of biotinylated transferrin (prepared by the method of Schryvers using Biotin-S-S-NHS from Pierce as the biotinylation reagent) is mixed with 25 mg total membrane protein from gonococcal strain FA19 in 25 ml of 100 mM NaCl/50 mM Tris, pH 8.0. The mixture is incubated at room temperature for 1 hour with gentle agitation. The membranes are pelletted at 17,000×g for 10 minutes. Pellets are resuspended in 25 ml of 100 mM NaCl/50 mM Tris, pH 8.0, followed by addition of $NA_2EDTA$ to a final concentration of 10 mM and N-lauroyl-sarcosine to a final concentration of 0.75%. Membranes are solubilized for 10 minutes at room temperature with agitation. 2.5 ml of streptavidin-agarose (Sigma) is added and is allowed to bind for 1 hour at room temperature. The resin is spun out at 3000×g for 5 minutes, the supernatant is removed and the resin is washed twice in 1M NaCl/50 mM Tris, pH 8.0 with 5 mM EDTA and 0.5% N-lauroyl-sarcosine and then twice in 1M NaCl/50 mM Tris, pH 8.0 with no additions. Protein is eluted from the matrix with 0.45% N-lauroyl-sarcosine and 125 mM beta-mercaptoethanol in 1M NaCl/50 mM Tris, pH 8.0.

2b. Affinity Purification of Meningococcal Transferrin-binding Protein

The procedure of example 2a is repeated, except meningococcal strain FAM20 is substituted for gonococcal strain FA19.

3a. Isolation of Gonococcal Transferrin-binding Protein

The eluate from the affinity preparation (Example 2a) is concentrated using Amicon concentrators (30,000 MW cut-off). The resulting concentrated protein preparation is solubilized in 20% glycerol, 4% SDS, 130 mM Tris, pH 8.0, 10 µg/ml bromophenol blue and separated on a 7.5% SDS polyacrylamide gel according to the method of Laemmli, Nature, 227, 680-685 (1970). The gel is stained with Coomassie Brilliant Blue to visualize the proteins. Two protein species are resolved as single bands by this method. Transferrin has a molecular weight of approximately 80 kD. The transferrin-binding protein has a molecular weight of 100 kD. The 100 kD protein band is excised, lyophilized and macerated.

3b. Isolation of Meningococcal Transferrin-binding Protein

The procedure of example 3A is repeated, except the eluate from example 2b is substituted for the eluate of example 2a.

4. Antisera against the Transferrin-binding Protein

The fine powders resulting from examples 3a and 3b are separately resuspended in saline, mixed with an equal volume of Freund's adjuvant (complete for the first injection; incomplete for subsequent injections) and injected into New England White, female rabbits. Injections are spaced two weeks apart. Anti-100 kD protein antibody can be detected two weeks after the third injection by western blotting against purified transferrin-binding protein.

5a. Gonococcal DNA Lambda-gt11 Expression Library

Chromosomal DNA from gonococcal strain FA19 is isolated according to Seifert et al, J. Bacteriol. 172, 40-46 (1990) and sonicated by standard procedures (Maniatis et al, 1982) to yield an average fragment size of 500 bp. EcoRI linkers are added and the resulting fragments are ligated into EcoRI digested lambda-gt11 DNA (Maniatis et al, 1982). Ligated DNA is packaged using a kit manufactured by Promega.

5b. Meningococcal DNA Lambda-gt11 Expression Library

Chromosomal DNA from meningococcal strain FAM20 is isolated in accordance with Seifert et al, J. Bacteriol. 172, 40-46 (1990) and digested with the restriction endonuclease HincII. EcoRI linkers are added, and the resultant DNA molecule is digested with EcoRI and ligated into EcoRI digested lambda-Zap (Stratagene). Ligated DNA is packaged using a kit manufactured by Promega.

6a. Immunological Screening of the Expression Library

Approximately 500,000 plaques obtained from the library of examples 5a and 5b are screened by the immunological screening method described in Stratagene's protocol accompanying the Picoblue Immunological Screening Kit. Briefly, the primary antisera is absorbed with an E. coli/phage lysate available from Stratagene (LaJolla, Calif.) according to their protocol. Approximately $5 \times 10^4$ pfu (plaque forming units) are plated on the E. coli host strain, Y1090. Nitrocellulose filters, soaked in 10 mM isopropylthiogalactoside (IPTG) are laid upon plates following 3-4 hours incubation at 42° C. Plates are then incubated overnight after which filters are removed, washed in tris-buffered saline and 0.05% Tween-20 (TBST) and blocked for one hour in tris-buffered saline and 5% bovine serum albumen. The filters are then incubated with a 1:200 dilution of the absorbed primary antibody for one hour. After incubation with primary antibody, filters are washed extensively with TBST and then incubated with the secondary antibody (1:3000 dilution of goat anti-rabbit antibody conjugated to alkaline phosphatase, purchased from Bio-Rad) for one hour. Filters are then washed extensively with TBST and finally incubated in 0.3 mg/ml nitroblue tetrazolium (NBT), 0.15 mg/ml 5-bromo-4-chloro-3-indoyl phosphate (BCIP), 100 mM Tris pH 9.8, 100 mM NaCl, 5 mM MgCl$_2$ until sufficient color develops.

Plaques which bind the transferrin-binding protein specific antisera are picked and purified away from other non-reacting plaques. The DNA from purified phage is isolated and purified using anion-exchange chromatography (column purchased from Qiagen, Studio City, Calif.).

6b. Screening the Expression Library with DNA Probes

Plaques obtained from the library of examples 5a and 5b are also screened using labeled DNA probes. Oligomer TfBP1, 2, 3, or 5 is labeled nonradioactively using digoxigenin-11-dUTP and a DNA tailing kit, both manufactured by Boehringer Mannheim Biochemicals (BMB).The sequences of the oligomers are:

TFBP1: GAG CCC GCC AAT GCG CCG CT (SEQ ID NO:8)

TFBP2: AGC GGC GCA TTG GCG GGC TC (SEQ ID NO:9)

TFBP3: GGG GCG CAT CGG CGG TGC GG (SEQ ID NO:10)

TFBP5: AAA ACA GTT GGA TAC CAT AC (SEQ ID NO:11)

The protocol for DNA labeling and detection are available from BMB with the Genius Nonradioactive DNA Labeling and Detecting Kit. Alternatively, the same oligomers are labeled radioactively with alpha $^{32}$P-dCTP and BMB's DNA tailing kit using standard techniques (Maniatis et al, 1982).

7. Amplification and Sequencing of DNA

The DNA obtained in example 5 or 6 is amplified by the PCR technique (Sambrook et al, (eds), Molecular Cloning: A Laboratory Manual, Second Edition. Cold Spring Harbor Press (1989)) using lambda-gt11-specific oligomers as amplimers. Inserts thus amplified are cloned into Bluescript vectors (Stratagene) using standard techniques (Maniatis et al, 1982) and sequenced by the dideoxy chain terminating method of Sanger et al, Proc. Natl. Acad. Sci USA 74, 5463-5467 (1977) using Sequenase (United States Biochemical Corp., Cleveland, Ohio). See SEQ ID NO:1.

8. Additional Sequence of the 100 kD Transferrin Binding Protein Gene from Gonococcal Strain FA19

Using the general methods of examples 6 and 7, a chromosomal Sau3AI fragment of approximately 1.0 kbp is identified. This fragment is cloned into the BamHI site of the vector pHSS6-GCU (Elkins et al. J. Bacteriol, 173, 3911-3913 (1991)). (The GCU designation indicates that a 10 bp sequence, known as the gonococcal uptake sequence, is included in the vector.) This sequence is known to mediate species-specific uptake of DNA into the gonococcus (Elkins et al., Id.). The host strain for this cloning is HB101. The resulting clone is known as pUNCH 403.

The insert in pUNCH 403 is sequenced in its entirety using double stranded templates prepared according to the method described by Kraft et al. in Biotechniques 6, 554-556 (1988). The sequence is determined by means of Sanger's dideoxy method using Sequenase®(United States Biochemicals).

9. Evidence of Structure and Function of the 100 kD Transferrin Binding Protein

To determine the effect of inactivation of the 100 kD transferrin binding protein gene, transposon insertions are isolated along the length of the insert in pUNCH403 according to the protocol described by Seifert et al, in Genetic Engineering, Principals and Methods, Setlow, J. K. and Holleander, A., eds., Plenum Press, N.Y., Vol. 8, pages 123-134. mTn3CAT transposons are inserted by shuttle mutagenesis in *E. coli*, and chloramphenicol resistant transformants are then selected in FA19 to create mutants. mTn3CAT transposons are referred to by Seifert et al. as m-Tn3(Cm). Mutants are then scored for their ability to grow on transferrin as their sole iron source and their ability to express the 100 kD protein as assayed by Western blot. The results of that experiment are shown in FIG. 3. Transposons at positions designated "I", 44, 37, and 24 ablate both expression of the 100 kD protein and its ability to grow on transferrin. The transposon at position "A", however, allowed some growth on transferrin and the expression of some detectable native length transferrin binding protein. These results confirm the hypothesis that the structural gene encoding the 100 kD protein begins at position 406, since an insertion upstream of this point allows expression of the wild-type length protein. The fact that expression is not detected at wild-type levels in mutant "A" indicates that the region upstream of the putative start codon is important for regulation of the gene encoding the 100 kD protein.

10. The Construction and Screening of Meningococcal Genomic Library

The 95 kD meningococcal transferrin binding protein gene is cloned in three steps. In the first step, using gonococcal anti-100 kD protein antibody, a 1.3 kb HincII/EcoRI fragment from a lambda Zap II (Stratagene) library is identified (see FIG. 4). The antigen used to generate the antibody is described in Example 4. The method for screening the library is described in Example 6a. The 1.3 kb fragment contains about 500 bp of the 95 kd protein structural gene. This clone hybridizes to a single 5 kb ClaI fragment in the meningococcal strain FAM20 chromosome. A partial 5 kb ClaI library in the vector pHSS6-GCU is constructed, and a 5 kb ClaI/ClaI fragment is cloned using the 1.3 kb fragment as a probe. In step 3, a 1.7 kb EcoRI/ClaI fragment (generated from the 5 kb ClaI fragment obtained in step 2) is used as a probe, resulting in the cloning of the adjacent HincII fragment from a lambda Zap II library. This EcoRI/HincII fragment is about 2.0 kb in size. Fragments generated from the 2.0 kb EcoRI/HincII fragment are used as probes to screen the lambda Zap II library, resulting in the clone shown in step 4, which contains the 3' end of the gene encoding the 95 kd transferrin-binding protein. The fragments shown in steps 1, 3 and 4 are sequenced by generating unidirectional deletions using Exonuclease III and VII as described by E. Ozkaynak and S. D. Putney in Biotechniques 5, 770 (1987). The complete DNA sequence of the structural gene encoding meningococcal TBP1 as determined from these fragments is shown in FIG. 5 and SEQ ID NO. 3.

11. Evidence of Structure and Function of the 95 kD Transferrin Binding Protein

The 1.3 kb HincII/EcoRI fragment is used to mutagenize the meningococcal 95 kD protein gene. The same shuttle mutagenesis procedure described in example 9 is employed, except that, instead of mTn3CAT transposons, mTn3erm transposons are introduced into the 1.3 kb clone. mTn3erm transposons are made by modifying the mTn3CAT transposons described in example 9 so as to confer erythromycin resistance. This modification permits erythromycin resistant meningococcal transformants to be selected. These transformants are screened for their ability to grow on transferrin plates as described in example 9. Results of this mutagenesis experiments are detailed in FIG. 6. While mTn3erm insertions 1 and 2 completely abolished the expression of the 95 kD protein and the ability of the clones to grown on transferrin plates, mTn3erm insertions 3 and 4 exhibited some growth on transferrin and showed some amount of 95 kD protein on Western blots. Based on the sequencing and mutagenesis data it appears that the mTn3erm insertions 1 and 2 are in the structural gene and promoter region, respectively, while insertions 3 and 4 seem to be in an upstream region that might be involved in the positive regulation of expression.

SUPPLEMENTAL REFERENCES

The invention as claimed is enabled in accordance with the specification and readily available references and starting materials. Nevertheless, the following cell lines have been deposited in the American Type Culture Collection, Bethesda, Md. on Jul. 16, 1990 in order to facilitate the making and using of the invention:

Meningococcal cell line FAM18 (Accession Number ATCC 55071)

Meningococcal cell line FAM20 (Accession Number ATCC 55072)

Gonococcal cell line FA19 (Accession Number ATCC 55073)

In addition, the following brochures containing useful protocols and information are available in the file history of this specification.

"Predigested Lambda Zap/Eco RI Cloning Kit Instruction Manual," Stratagene, La Jolla, Calif. (Nov. 20, 1987);

"Gigapack Plus" (for packaging recombinant lambda phage), Stratagene, La Jolla, Calif. (Apr. 25, 1988);

"picoBlue Immunoscreening Kit" Instruction Manual," Stratagene, La Jolla, Calif., (May 19, 1989); and "Genius Nonradioactive DNA Labeling and Detection Kit," Boehringer Mannheim Biochemicals, Indianapolis, Ind. (January, 1989).

The invention claimed is:

1. An isolated protein comprising the sequence of SEQ ID NO:2.

\* \* \* \* \*

SEQUENCE LISTING

```
<160> NUMBER OF SEQ ID NOS: 4

<210> SEQ ID NO 1
<211> LENGTH: 3286
<212> TYPE: DNA
<213> ORGANISM: Neisseria gonorrhoeae
```

```
<220> FEATURE:
<221> NAME/KEY: CDS
<222> LOCATION: (406)..(3150)

<400> SEQUENCE: 1
aaccgctgaa aacaggtcgg aggcaacctt taccattgac gccatgattg agggcaacgg      60
ctttaaaggt acggcgaaaa ccggtaatga cggatttgcg ccggatcaaa acaatagcac     120
cgttacacat aaagtgcaca tcgcaaatgc cgaagtgcag gcggttttt acgggcctaa     180 cgccgaagag ttgggcggat ggtttgccta tccgggcaat gaacaaacga aaaatgcaac     240
agttgaatcc ggcaatggaa attcagcaag cagtgcaact gtcgtattcg gtgcgaaacg     300
ccaaaagctt gtgaaataag cacggctgcc gaacaatcga gaataaggct tcagacggca     360
tcgttccttc cgattccgtc tgaaagcgaa gattagggaa acact atg caa cag caa     417
                                              Met Gln Gln Gln
                                                1 cat ttg ttc cga tta aat att tta tgc ctg tct tta atg act gcg ctg        465
His Leu Phe Arg Leu Asn Ile Leu Cys Leu Ser Leu Met Thr Ala Leu
  5                  10                  15                  20 ccc gct tat gca gaa aat gtg caa gcc gga caa gca cag gaa aaa cag        513
Pro Ala Tyr Ala Glu Asn Val Gln Ala Gly Gln Ala Gln Glu Lys Gln
             25                  30                  35 ttg gat acc ata cag gta aaa gcc aaa aaa cag aaa acc cgc cgc gat        561
Leu Asp Thr Ile Gln Val Lys Ala Lys Lys Gln Lys Thr Arg Arg Asp
         40                  45                  50 aac gaa gta acc ggt ttg ggc aaa ttg gtc aaa acc gcc gac acc ctc        609
Asn Glu Val Thr Gly Leu Gly Lys Leu Val Lys Thr Ala Asp Thr Leu
     55                  60                  65 agc aag gaa cag gta ctc gac atc cgc gac ctg acg cgt tac gac ccc        657
Ser Lys Glu Gln Val Leu Asp Ile Arg Asp Leu Thr Arg Tyr Asp Pro
 70                  75                  80 ggc atc gcc gtc gtc gaa cag ggg cgc ggc gca agc tcg ggc tac tcg        705
Gly Ile Ala Val Val Glu Gln Gly Arg Gly Ala Ser Ser Gly Tyr Ser
 85                  90                  95                 100 ata cgc ggt atg gac aaa aac cgc gtc tcc ttg acg gtg gac ggc ttg        753
Ile Arg Gly Met Asp Lys Asn Arg Val Ser Leu Thr Val Asp Gly Leu
                105                 110                 115 gcg caa ata cag tcc tac acc gcg cag gcg gca ttg ggc ggg acg agg        801
Ala Gln Ile Gln Ser Tyr Thr Ala Gln Ala Ala Leu Gly Gly Thr Arg
            120                 125                 130 acg gcg ggc agc agc ggc gca atc aat gaa atc gag tat gag aac gtc        849
Thr Ala Gly Ser Ser Gly Ala Ile Asn Glu Ile Glu Tyr Glu Asn Val
        135                 140                 145 aag gct gtc gaa atc agc aaa ggc tca aac tcg gtc gaa caa ggc agc        897
Lys Ala Val Glu Ile Ser Lys Gly Ser Asn Ser Val Glu Gln Gly Ser
    150                 155                 160 ggc gca ttg gcg ggc tcg gtc gca ttt caa acc aaa acc gcc gac gat        945
Gly Ala Leu Ala Gly Ser Val Ala Phe Gln Thr Lys Thr Ala Asp Asp
165                 170                 175                 180 gtt atc ggg gaa ggc agg cag tgg ggc att cag agt aaa acc gcc tat        993
Val Ile Gly Glu Gly Arg Gln Trp Gly Ile Gln Ser Lys Thr Ala Tyr
                185                 190                 195 tcc ggc aaa aac cgg ggg ctt acc caa tcc atc gcg ctg gcg ggg cgc       1041
Ser Gly Lys Asn Arg Gly Leu Thr Gln Ser Ile Ala Leu Ala Gly Arg
            200                 205                 210 atc ggc ggt gcg gag gct ttg ctg atc cgc acc ggg cgg cac gcg ggg       1089
Ile Gly Gly Ala Glu Ala Leu Leu Ile Arg Thr Gly Arg His Ala Gly
        215                 220                 225
```

```
gaa atc cgc gcc cac gaa gcc gcc gga cgc ggc gtt cag agc ttc aac    1137
Glu Ile Arg Ala His Glu Ala Ala Gly Arg Gly Val Gln Ser Phe Asn
    230                 235                 240 agg ctg gcg ccg gtt gat gac ggc agc aag tac gcc tat ttc atc gtt    1185
Arg Leu Ala Pro Val Asp Asp Gly Ser Lys Tyr Ala Tyr Phe Ile Val
245                 250                 255                 260 gaa gaa gaa tgc aaa aac ggg ggt cac gaa aag tgt aaa gcg aat ccg    1233
Glu Glu Glu Cys Lys Asn Gly Gly His Glu Lys Cys Lys Ala Asn Pro
                265                 270                 275 aaa aaa gat gtt gtc ggc gaa gac aaa cgt caa acg gtt tcc acc cga    1281
Lys Lys Asp Val Val Gly Glu Asp Lys Arg Gln Thr Val Ser Thr Arg
            280                 285                 290 gac tac acg ggc ccc aac cgc ttc ctc gcc gat ccg ctt tca tac gaa    1329
Asp Tyr Thr Gly Pro Asn Arg Phe Leu Ala Asp Pro Leu Ser Tyr Glu
        295                 300                 305 agc cgg tcg tgg ctg ttc cgc ccg ggt ttt cgt ttt gaa aac aaa cgg    1377
Ser Arg Ser Trp Leu Phe Arg Pro Gly Phe Arg Phe Glu Asn Lys Arg
    310                 315                 320 cac tac atc ggc ggc ata ctc gaa cgc acg caa caa act ttc gac acg    1425
His Tyr Ile Gly Gly Ile Leu Glu Arg Thr Gln Gln Thr Phe Asp Thr
325                 330                 335                 340 cgc gat atg acg gtt ccg gca ttt ctg acc aag gcg gtt ttt gat gca    1473
Arg Asp Met Thr Val Pro Ala Phe Leu Thr Lys Ala Val Phe Asp Ala
                345                 350                 355 aat caa aaa cag gcg ggt tct ttg cgc ggc aac ggc aaa tac gcg ggc    1521
Asn Gln Lys Gln Ala Gly Ser Leu Arg Gly Asn Gly Lys Tyr Ala Gly
            360                 365                 370 aac cac aaa tac ggc gga ctg ttt acc agc ggc gaa aac aat gcg ccg    1569
Asn His Lys Tyr Gly Gly Leu Phe Thr Ser Gly Glu Asn Asn Ala Pro
        375                 380                 385 gtg ggc gcg gaa tac ggt acg ggc gtg ttt tac gac gag acg cac acc    1617
Val Gly Ala Glu Tyr Gly Thr Gly Val Phe Tyr Asp Glu Thr His Thr
    390                 395                 400 aaa agc cgc tac ggt ttg gaa tat gtc tat acc aat gcc gat aaa gac    1665
Lys Ser Arg Tyr Gly Leu Glu Tyr Val Tyr Thr Asn Ala Asp Lys Asp
405                 410                 415                 420 act tgg gcg gat tat gcc cgc ctc tct tac gac cgg cag ggc atc ggt    1713
Thr Trp Ala Asp Tyr Ala Arg Leu Ser Tyr Asp Arg Gln Gly Ile Gly
                425                 430                 435 ttg gac aac cat ttt cag cag acg cac tgt tcc gcc gac ggt tcg gac    1761
Leu Asp Asn His Phe Gln Gln Thr His Cys Ser Ala Asp Gly Ser Asp
            440                 445                 450 aaa tat tgc cgt ccg agt gcc gac aag ccg ttt tcc tat tac aaa tcc    1809
Lys Tyr Cys Arg Pro Ser Ala Asp Lys Pro Phe Ser Tyr Tyr Lys Ser
        455                 460                 465 gac cgc gtg att tac ggg gaa agc cat aag ctc ttg cag gcg gca ttc    1857
Asp Arg Val Ile Tyr Gly Glu Ser His Lys Leu Leu Gln Ala Ala Phe
    470                 475                 480 aaa aaa tcc ttc gat acc gcc aaa atc cgc cac aac ctg agc gtg aat    1905
Lys Lys Ser Phe Asp Thr Ala Lys Ile Arg His Asn Leu Ser Val Asn
485                 490                 495                 500 ctc ggt tac gac cgc ttc ggc tct aat ctc cgc cat cag cat tat tat    1953
Leu Gly Tyr Asp Arg Phe Gly Ser Asn Leu Arg His Gln His Tyr Tyr
                505                 510                 515 tat caa agt gcc aac cgc gcc tat tcg ttg aaa acg ccc cct caa aac    2001
Tyr Gln Ser Ala Asn Arg Ala Tyr Ser Leu Lys Thr Pro Pro Gln Asn
            520                 525                 530 aac ggc aaa aaa acc agc ccc aac gga aga gaa aag aat ccc tat tgg    2049
Asn Gly Lys Lys Thr Ser Pro Asn Gly Arg Glu Lys Asn Pro Tyr Trp
        535                 540                 545
```

```
                                                                            -continued gtc agc ata ggc agg gga aat gtc gtt acg agg caa atc tgc ctc ttt              2097
Val Ser Ile Gly Arg Gly Asn Val Val Thr Arg Gln Ile Cys Leu Phe
    550                 555                 560 ggc aac aat act tat acg gac tgc acg ccg cgc agc atc aac ggc aaa              2145
Gly Asn Asn Thr Tyr Thr Asp Cys Thr Pro Arg Ser Ile Asn Gly Lys
565                 570                 575                 580 agc tat tac gcg gcg gtc cgg gac aat gtc cgt ttg ggc agg tgg gcg              2193
Ser Tyr Tyr Ala Ala Val Arg Asp Asn Val Arg Leu Gly Arg Trp Ala
                585                 590                 595 gat gtc ggc gcg ggc ttg cgc tac gac tac cgc agc acg cat tcg gac              2241
Asp Val Gly Ala Gly Leu Arg Tyr Asp Tyr Arg Ser Thr His Ser Asp
            600                 605                 610 gac ggc agc gtt tcc acc ggc acg cac cgc acc ctg tcc tgg aac gcc              2289
Asp Gly Ser Val Ser Thr Gly Thr His Arg Thr Leu Ser Trp Asn Ala
        615                 620                 625 ggc atc gtc ctc aaa cct gcc gac tgg ctg gat ttg act tac cgc act              2337
Gly Ile Val Leu Lys Pro Ala Asp Trp Leu Asp Leu Thr Tyr Arg Thr
    630                 635                 640 tca acc ggc ttc cgc ctg ccc tcg ttt gcg gaa atg tac ggc tgg cgg              2385
Ser Thr Gly Phe Arg Leu Pro Ser Phe Ala Glu Met Tyr Gly Trp Arg
645                 650                 655                 660 tcg ggc gat aaa ata aaa gcc gtc aaa atc gat ccg gaa aaa tcg ttc              2433
Ser Gly Asp Lys Ile Lys Ala Val Lys Ile Asp Pro Glu Lys Ser Phe
                665                 670                 675 aac aaa gaa gcc ggc atc gtg ttt aaa ggc gat ttc ggc aac ttg gag              2481
Asn Lys Glu Ala Gly Ile Val Phe Lys Gly Asp Phe Gly Asn Leu Glu
            680                 685                 690 gca agt tgg ttc aac aat gcc tac cgc gat ttg att gtc cgg ggt tat              2529
Ala Ser Trp Phe Asn Asn Ala Tyr Arg Asp Leu Ile Val Arg Gly Tyr
        695                 700                 705 gaa gcg caa att aaa gac ggc aaa gaa caa gtc aaa ggc aac ccg gct              2577
Glu Ala Gln Ile Lys Asp Gly Lys Glu Gln Val Lys Gly Asn Pro Ala
    710                 715                 720 tac ctc aat gcc caa agc gcg cgg att acc ggc atc aat att ttg ggc              2625
Tyr Leu Asn Ala Gln Ser Ala Arg Ile Thr Gly Ile Asn Ile Leu Gly
725                 730                 735                 740 aaa atc gat tgg aac ggc gta tgg gat aaa ttg ccc gaa ggt tgg tat              2673
Lys Ile Asp Trp Asn Gly Val Trp Asp Lys Leu Pro Glu Gly Trp Tyr
                745                 750                 755 tcc aca ttt gcc tat aat cgt gtc cgt gtc cgc gac atc aaa aaa cgc              2721
Ser Thr Phe Ala Tyr Asn Arg Val Arg Val Arg Asp Ile Lys Lys Arg
            760                 765                 770 gca gac cgc acc gat att caa tca cac ctg ttt gat gcc atc caa ccc              2769
Ala Asp Arg Thr Asp Ile Gln Ser His Leu Phe Asp Ala Ile Gln Pro
        775                 780                 785 tcg cgc tat gtc gtc ggc tcg ggc tat gac caa ccg gaa ggc aaa tgg              2817
Ser Arg Tyr Val Val Gly Ser Gly Tyr Asp Gln Pro Glu Gly Lys Trp
    790                 795                 800 ggc gtg aac ggt atg ctg act tat tcc aaa gcc aag gaa atc aca gag              2865
Gly Val Asn Gly Met Leu Thr Tyr Ser Lys Ala Lys Glu Ile Thr Glu
805                 810                 815                 820 ttg ttg ggc agc cgg gct ttg ctc aac ggc aac agc cgc aat aca aaa              2913
Leu Leu Gly Ser Arg Ala Leu Leu Asn Gly Asn Ser Arg Asn Thr Lys
                825                 830                 835 gcc acc gcg cgc cgt acc cgc cct tgg tat att gtg gac gtg tcc ggt              2961
Ala Thr Ala Arg Arg Thr Arg Pro Trp Tyr Ile Val Asp Val Ser Gly
            840                 845                 850 tat tac acg gtt aaa aaa cac ttc acc ctc cgt gcg ggc gtg tac aac              3009
Tyr Tyr Thr Val Lys Lys His Phe Thr Leu Arg Ala Gly Val Tyr Asn
        855                 860                 865
```

-continued

| | | | | | | | | | | | | | | |
|---|---|---|---|---|---|---|---|---|---|---|---|---|---|---|
| ctc | ctc | aac | cac | cgc | tat | gtt | act | tgg | gaa | aat | gtg | cgg | caa | act | gcc | 3057 |
| Leu | Leu | Asn | His | Arg | Tyr | Val | Thr | Trp | Glu | Asn | Val | Arg | Gln | Thr | Ala |
| | 870 | | | | 875 | | | | | 880 | | | | |

| gcc | ggc | gca | gtc | aac | caa | cac | aaa | aat | gtc | ggc | gtt | tac | aac | cga | tat | 3105 |
| Ala | Gly | Ala | Val | Asn | Gln | His | Lys | Asn | Val | Gly | Val | Tyr | Asn | Arg | Tyr |
| 885 | | | | | 890 | | | | | 895 | | | | | 900 |

| gcc | gcc | ccc | ggc | cgc | aac | tac | aca | ttt | agc | ttg | gaa | atg | aag | ttc | | 3150 |
| Ala | Ala | Pro | Gly | Arg | Asn | Tyr | Thr | Phe | Ser | Leu | Glu | Met | Lys | Phe |
| | | | 905 | | | | | 910 | | | | | 915 | taaacgtccg aacgccgcaa atgccgtctg aaaggcttca gacggcgttt tttttacaca 3210 atccccaccg tttcccatcc ttcccgatac accgtaatcc cgaaaccgt cattcccgcg 3270 caggcgtgca tccggg 3286

<210> SEQ ID NO 2
<211> LENGTH: 915
<212> TYPE: PRT
<213> ORGANISM: Neisseria gonorrhoeae

<400> SEQUENCE: 2

Met Gln Gln Gln His Leu Phe Arg Leu Asn Ile Leu Cys Leu Ser Leu
1               5                   10                  15

Met Thr Ala Leu Pro Ala Tyr Ala Glu Asn Val Gln Ala Gly Gln Ala
            20                  25                  30

Gln Glu Lys Gln Leu Asp Thr Ile Gln Val Lys Ala Lys Lys Gln Lys
        35                  40                  45

Thr Arg Arg Asp Asn Glu Val Thr Gly Leu Gly Lys Leu Val Lys Thr
    50                  55                  60

Ala Asp Thr Leu Ser Lys Glu Gln Val Leu Asp Ile Arg Asp Leu Thr
65                  70                  75                  80

Arg Tyr Asp Pro Gly Ile Ala Val Val Glu Gln Gly Arg Gly Ala Ser
                85                  90                  95

Ser Gly Tyr Ser Ile Arg Gly Met Asp Lys Asn Arg Val Ser Leu Thr
            100                 105                 110

Val Asp Gly Leu Ala Gln Ile Gln Ser Tyr Thr Ala Gln Ala Ala Leu
        115                 120                 125

Gly Gly Thr Arg Thr Ala Gly Ser Ser Gly Ala Ile Asn Glu Ile Glu
    130                 135                 140

Tyr Glu Asn Val Lys Ala Val Glu Ile Ser Lys Gly Ser Asn Ser Val
145                 150                 155                 160

Glu Gln Gly Ser Gly Ala Leu Ala Gly Ser Val Ala Phe Gln Thr Lys
                165                 170                 175

Thr Ala Asp Asp Val Ile Gly Glu Gly Arg Gln Trp Gly Ile Gln Ser
            180                 185                 190

Lys Thr Ala Tyr Ser Gly Lys Asn Arg Gly Leu Thr Gln Ser Ile Ala
        195                 200                 205

Leu Ala Gly Arg Ile Gly Gly Ala Glu Ala Leu Leu Ile Arg Thr Gly
    210                 215                 220

Arg His Ala Gly Glu Ile Arg Ala His Glu Ala Ala Gly Arg Gly Val
225                 230                 235                 240

Gln Ser Phe Asn Arg Leu Ala Pro Val Asp Asp Gly Ser Lys Tyr Ala
                245                 250                 255

Tyr Phe Ile Val Glu Glu Glu Cys Lys Asn Gly Gly His Glu Lys Cys
            260                 265                 270

Lys Ala Asn Pro Lys Lys Asp Val Val Gly Glu Asp Lys Arg Gln Thr
        275                 280                 285

-continued

```
Val Ser Thr Arg Asp Tyr Thr Gly Pro Asn Arg Phe Leu Ala Asp Pro
    290                 295                 300

Leu Ser Tyr Glu Ser Arg Ser Trp Leu Phe Arg Pro Gly Phe Arg Phe
305                 310                 315                 320

Glu Asn Lys Arg His Tyr Ile Gly Gly Ile Leu Glu Arg Thr Gln Gln
                325                 330                 335

Thr Phe Asp Thr Arg Asp Met Thr Val Pro Ala Phe Leu Thr Lys Ala
            340                 345                 350

Val Phe Asp Ala Asn Gln Lys Gln Ala Gly Ser Leu Arg Gly Asn Gly
        355                 360                 365

Lys Tyr Ala Gly Asn His Lys Tyr Gly Gly Leu Phe Thr Ser Gly Glu
    370                 375                 380

Asn Asn Ala Pro Val Gly Ala Glu Tyr Gly Thr Gly Val Phe Tyr Asp
385                 390                 395                 400

Glu Thr His Thr Lys Ser Arg Tyr Gly Leu Glu Tyr Val Tyr Thr Asn
                405                 410                 415

Ala Asp Lys Asp Thr Trp Ala Asp Tyr Ala Arg Leu Ser Tyr Asp Arg
            420                 425                 430

Gln Gly Ile Gly Leu Asp Asn His Phe Gln Gln Thr His Cys Ser Ala
        435                 440                 445

Asp Gly Ser Asp Lys Tyr Cys Arg Pro Ser Ala Asp Lys Pro Phe Ser
    450                 455                 460

Tyr Tyr Lys Ser Asp Arg Val Ile Tyr Gly Glu Ser His Lys Leu Leu
465                 470                 475                 480

Gln Ala Ala Phe Lys Lys Ser Phe Asp Thr Ala Lys Ile Arg His Asn
                485                 490                 495

Leu Ser Val Asn Leu Gly Tyr Asp Arg Phe Gly Ser Asn Leu Arg His
            500                 505                 510

Gln His Tyr Tyr Gln Ser Ala Asn Arg Ala Tyr Ser Leu Lys Thr
        515                 520                 525

Pro Pro Gln Asn Asn Gly Lys Lys Thr Ser Pro Asn Gly Arg Glu Lys
    530                 535                 540

Asn Pro Tyr Trp Val Ser Ile Gly Arg Gly Asn Val Val Thr Arg Gln
545                 550                 555                 560

Ile Cys Leu Phe Gly Asn Asn Thr Tyr Thr Asp Cys Thr Pro Arg Ser
                565                 570                 575

Ile Asn Gly Lys Ser Tyr Ala Ala Val Arg Asp Asn Val Arg Leu
            580                 585                 590

Gly Arg Trp Ala Asp Val Gly Ala Gly Leu Arg Tyr Asp Tyr Arg Ser
        595                 600                 605

Thr His Ser Asp Asp Gly Ser Val Ser Thr Gly Thr His Arg Thr Leu
    610                 615                 620

Ser Trp Asn Ala Gly Ile Val Leu Lys Pro Ala Asp Trp Leu Asp Leu
625                 630                 635                 640

Thr Tyr Arg Thr Ser Thr Gly Phe Arg Leu Pro Ser Phe Ala Glu Met
                645                 650                 655

Tyr Gly Trp Arg Ser Gly Asp Lys Ile Lys Ala Val Lys Ile Asp Pro
            660                 665                 670

Glu Lys Ser Phe Asn Lys Glu Ala Gly Ile Val Phe Lys Gly Asp Phe
        675                 680                 685

Gly Asn Leu Glu Ala Ser Trp Phe Asn Asn Ala Tyr Arg Asp Leu Ile
    690                 695                 700
```

| | | | | | | | | | | | |
|---|---|---|---|---|---|---|---|---|---|---|---|
| Val | Arg | Gly | Tyr | Glu | Ala | Gln | Ile | Lys | Asp | Gly | Lys | Glu | Gln | Val | Lys |
| 705 | | | | 710 | | | | 715 | | | | 720 | | | |

Val Arg Gly Tyr Glu Ala Gln Ile Lys Asp Gly Lys Glu Gln Val Lys
705                 710                 715                 720

Gly Asn Pro Ala Tyr Leu Asn Ala Gln Ser Ala Arg Ile Thr Gly Ile
                725                 730                 735

Asn Ile Leu Gly Lys Ile Asp Trp Asn Gly Val Trp Asp Lys Leu Pro
            740                 745                 750

Glu Gly Trp Tyr Ser Thr Phe Ala Tyr Asn Arg Val Arg Val Arg Asp
        755                 760                 765

Ile Lys Lys Arg Ala Asp Arg Thr Asp Ile Gln Ser His Leu Phe Asp
    770                 775                 780

Ala Ile Gln Pro Ser Arg Tyr Val Val Gly Ser Gly Tyr Asp Gln Pro
785                 790                 795                 800

Glu Gly Lys Trp Gly Val Asn Gly Met Leu Thr Tyr Ser Lys Ala Lys
                805                 810                 815

Glu Ile Thr Glu Leu Leu Gly Ser Arg Ala Leu Leu Asn Gly Asn Ser
            820                 825                 830

Arg Asn Thr Lys Ala Thr Ala Arg Arg Thr Arg Pro Trp Tyr Ile Val
        835                 840                 845

Asp Val Ser Gly Tyr Tyr Thr Val Lys Lys His Phe Thr Leu Arg Ala
    850                 855                 860

Gly Val Tyr Asn Leu Leu Asn His Arg Tyr Val Thr Trp Glu Asn Val
865                 870                 875                 880

Arg Gln Thr Ala Ala Gly Ala Val Asn Gln His Lys Asn Val Gly Val
                885                 890                 895

Tyr Asn Arg Tyr Ala Ala Pro Gly Arg Asn Tyr Thr Phe Ser Leu Glu
            900                 905                 910

Met Lys Phe
        915

<210> SEQ ID NO 3
<211> LENGTH: 3537
<212> TYPE: DNA
<213> ORGANISM: Neisseria meningitidis
<220> FEATURE:
<221> NAME/KEY: CDS
<222> LOCATION: (721)..(3447)

<400> SEQUENCE: 3

```
gaattccgac ggagtggagc tttcactgct gccgtctgag ggcaataagg cggcatttca      60
gcacgagatt gagcaaaacg gcgtgaaggc aacggtgtgt tgttccaact tggattacat     120
gagttttggg aagctgtcaa agaaaataa agacgtatg ttcctgcaag gtgtccgcac      180
tccagtatcc gatgtggcgg caaggacgga gcaaacgcca atatcgcgg tacttggtac     240 ggatatattg ccaacggcac aagctggagc gcgaagcctc caatcaggaa ggtggtaata     300
gggcagagtt tgacgtggat ttttccacta aaaaaatcag tggcacactg acggcaaaag     360
accgtacgtc tcctgcgttt actattactg ccatgattaa ggacaacggt ttttcaggtg     420
tggcgaaaac cggtgaaaac ggctttgcgc tggatccgca aaataccgga aattcccact     480
atacgcatat tgaagccact gtatccggcg gtttctacgg caaaaacgcc atcgagatgg     540
cggatcgttc tcatttccgg gaaatgcacc agagggaaaa caagaaaaag catcggtggt     600
attcggtcgg aaacgccaac agcttgtgca ataagcacg ctgccgaaca atcgagaata     660
aggcttcaga cggcaccgtt ccttccgatg ccgtctgaaa gcgaagatta gggaaacact     720
```

```
                                                                -continued atg caa cag caa cat ttg ttc cga tta aat att tta tgc ctg tct tta      768
Met Gln Gln Gln His Leu Phe Arg Leu Asn Ile Leu Cys Leu Ser Leu
 1               5                  10                  15 atg acc gcg ctg ccc gtt tat gca gaa aat gtg caa gcc gaa caa gca      816
Met Thr Ala Leu Pro Val Tyr Ala Glu Asn Val Gln Ala Glu Gln Ala
             20                  25                  30 cag gaa aaa cag ttg gat acc ata cag gta aaa gcc aaa aaa cag aaa      864
Gln Glu Lys Gln Leu Asp Thr Ile Gln Val Lys Ala Lys Lys Gln Lys
         35                  40                  45 acc cgc cgc gat aac gaa gta acc ggg ctg ggc aag ttg gtc aag tct      912
Thr Arg Arg Asp Asn Glu Val Thr Gly Leu Gly Lys Leu Val Lys Ser
     50                  55                  60 tcc gat acg cta agt aaa gaa cag gtt ttg aat atc cga gac ctg acc      960
Ser Asp Thr Leu Ser Lys Glu Gln Val Leu Asn Ile Arg Asp Leu Thr
 65                  70                  75                  80 cgt tat gat ccg ggt att gcc gtg gtc gaa cag ggt cgg ggc gca agt     1008
Arg Tyr Asp Pro Gly Ile Ala Val Val Glu Gln Gly Arg Gly Ala Ser
                 85                  90                  95 tcc ggc tat tca ata cgc ggc atg gat aaa aac cgc gtt tcc tta acg     1056
Ser Gly Tyr Ser Ile Arg Gly Met Asp Lys Asn Arg Val Ser Leu Thr
            100                 105                 110 gta gac ggc gtt tcg caa ata cag tcc tac acc gcg cag gcg gca ttg     1104
Val Asp Gly Val Ser Gln Ile Gln Ser Tyr Thr Ala Gln Ala Ala Leu
        115                 120                 125 ggt ggg acg agg acg gcg ggt agc agc ggc gca atc aat gaa atc gag     1152
Gly Gly Thr Arg Thr Ala Gly Ser Ser Gly Ala Ile Asn Glu Ile Glu
    130                 135                 140 tat gaa aac gtc aag gcc gtt gaa atc agc aag ggt tcg aat tca tca     1200
Tyr Glu Asn Val Lys Ala Val Glu Ile Ser Lys Gly Ser Asn Ser Ser
145                 150                 155                 160 gaa tac gga aac ggc gca ttg gca ggt tcg gtc gca ttt caa acc aaa     1248
Glu Tyr Gly Asn Gly Ala Leu Ala Gly Ser Val Ala Phe Gln Thr Lys
                165                 170                 175 acc gca gcc gac att atc gga gag gga aaa cag tgg ggc att cag agt     1296
Thr Ala Ala Asp Ile Ile Gly Glu Gly Lys Gln Trp Gly Ile Gln Ser
            180                 185                 190 aaa act gcc tat tcg gga aaa gac cat gcc ctg acg caa tcc ctt gcg     1344
Lys Thr Ala Tyr Ser Gly Lys Asp His Ala Leu Thr Gln Ser Leu Ala
        195                 200                 205 ctt gcc gga cgc agc ggc gcg gaa gcc ctc ctt att tat act aaa         1392
Leu Ala Gly Arg Ser Gly Gly Ala Glu Ala Leu Leu Ile Tyr Thr Lys
    210                 215                 220 cgg cgg ggt cgg gaa atc cat gcg cat aaa gat gcc ggc aag ggt gtg     1440
Arg Arg Gly Arg Glu Ile His Ala His Lys Asp Ala Gly Lys Gly Val
225                 230                 235                 240 cag agc ttc aac cgg ctg gtg ttg gac gag gac aag aag gag ggt ggc     1488
Gln Ser Phe Asn Arg Leu Val Leu Asp Glu Asp Lys Lys Glu Gly Gly
                245                 250                 255 agt cag tca gat att tca ttg tgc gaa gaa gaa tgc cac aat gga tat     1536
Ser Gln Ser Asp Ile Ser Leu Cys Glu Glu Glu Cys His Asn Gly Tyr
            260                 265                 270 gcg gcc tgt aaa aac aag ctg aaa gaa gat gcc tcg gtc aaa gat gag     1584
Ala Ala Cys Lys Asn Lys Leu Lys Glu Asp Ala Ser Val Lys Asp Glu
        275                 280                 285 cgc aaa acc gtc agc acg cag gat tat acc ggc tcc aac cgc tta ctt     1632
Arg Lys Thr Val Ser Thr Gln Asp Tyr Thr Gly Ser Asn Arg Leu Leu
    290                 295                 300 gcg aac ccg ctt gag tat ggc agc caa tca tgg ctg ttc cga ccg ggt     1680
Ala Asn Pro Leu Glu Tyr Gly Ser Gln Ser Trp Leu Phe Arg Pro Gly
305                 310                 315                 320
```

```
tgg cat ttg gac aac cgc cat tat gtc gga gcc gtt ctc gaa cgt acg      1728
Trp His Leu Asp Asn Arg His Tyr Val Gly Ala Val Leu Glu Arg Thr
            325             330             335 cag cag acc ttt gat aca cgg gat atg act gtt cct gcc tat ttt acc      1776
Gln Gln Thr Phe Asp Thr Arg Asp Met Thr Val Pro Ala Tyr Phe Thr
            340             345             350 agt gaa gat tat gta ccc ggt tcg ctg aaa ggt ctt ggc aaa tat tcg      1824
Ser Glu Asp Tyr Val Pro Gly Ser Leu Lys Gly Leu Gly Lys Tyr Ser
            355             360             365 ggc gat aat aag gca gaa agg ctg ttt gtt cag gga gag ggc agt aca      1872
Gly Asp Asn Lys Ala Glu Arg Leu Phe Val Gln Gly Glu Gly Ser Thr
            370             375             380 ttg cag ggt atc ggt tac ggt acc ggc gtg ttt tat gat gaa cgc cat      1920
Leu Gln Gly Ile Gly Tyr Gly Thr Gly Val Phe Tyr Asp Glu Arg His
385             390             395             400 act aaa aac cgc tac ggg gtc gaa tat gtt tac cat aat gct gat aag      1968
Thr Lys Asn Arg Tyr Gly Val Glu Tyr Val Tyr His Asn Ala Asp Lys
            405             410             415 gat acc tgg gcc gat tac gcc cga ctt tct tat gac cgg caa ggt ata      2016
Asp Thr Trp Ala Asp Tyr Ala Arg Leu Ser Tyr Asp Arg Gln Gly Ile
            420             425             430 gat ttg gac aac cgt ttg cag cag acg cat tgc tct cac gac ggt tcg      2064
Asp Leu Asp Asn Arg Leu Gln Gln Thr His Cys Ser His Asp Gly Ser
            435             440             445 gat aaa aat tgc cgt ccc gac ggc aat aaa ccg tat tct ttc tat aaa      2112
Asp Lys Asn Cys Arg Pro Asp Gly Asn Lys Pro Tyr Ser Phe Tyr Lys
450             455             460 tcc gac cgg atg att tat gaa gaa agc cga aac ctg ttc caa gca gta      2160
Ser Asp Arg Met Ile Tyr Glu Glu Ser Arg Asn Leu Phe Gln Ala Val
465             470             475             480 ttt aaa aag gca ttt gat acg gcc aaa atc cgt cac aat ttg agt atc      2208
Phe Lys Lys Ala Phe Asp Thr Ala Lys Ile Arg His Asn Leu Ser Ile
            485             490             495 aat cta ggg tac gac cgc ttt aag tcg caa ttg tcc cac agc gat tat      2256
Asn Leu Gly Tyr Asp Arg Phe Lys Ser Gln Leu Ser His Ser Asp Tyr
            500             505             510 tat ctt caa aac gca gtt cag gca tat gat ttg ata acc ccg aaa aag      2304
Tyr Leu Gln Asn Ala Val Gln Ala Tyr Asp Leu Ile Thr Pro Lys Lys
            515             520             525 cct ccg ttt ccc aac gga agc aaa gac aac ccg tat agg gtg tct atc      2352
Pro Pro Phe Pro Asn Gly Ser Lys Asp Asn Pro Tyr Arg Val Ser Ile
530             535             540 ggc aag acc acg gtc aat aca tcg ccg ata cct ggt ttc ggc aat aac      2400
Gly Lys Thr Thr Val Asn Thr Ser Pro Ile Pro Gly Phe Gly Asn Asn
545             550             555             560 acc tat aca gac tgc aca ccg agg aat atc ggc ggc aac ggt tat tat      2448
Thr Tyr Thr Asp Cys Thr Pro Arg Asn Ile Gly Gly Asn Gly Tyr Tyr
            565             570             575 gca gcc gtt caa gac aat gtc cgt ttg ggc agg tgg gcg gat gtc gga      2496
Ala Ala Val Gln Asp Asn Val Arg Leu Gly Arg Trp Ala Asp Val Gly
            580             585             590 gca ggc ata cgt tac gat tac cgc agc acg cat tcg gaa gat aag agt      2544
Ala Gly Ile Arg Tyr Asp Tyr Arg Ser Thr His Ser Glu Asp Lys Ser
            595             600             605 gtc tct acc ggc act cac cgc aac ctt tct tgg aac gcg ggc gta gtc      2592
Val Ser Thr Gly Thr His Arg Asn Leu Ser Trp Asn Ala Gly Val Val
            610             615             620 ctc aaa cct ttc acc tgg atg gat ttg act tat cgc gct tct acg ggc      2640
Leu Lys Pro Phe Thr Trp Met Asp Leu Thr Tyr Arg Ala Ser Thr Gly
625             630             635             640
```

```
ttc cgt ctg ccg tcg ttt gcc gaa atg tat ggc tgg aga gcc ggg gag    2688
Phe Arg Leu Pro Ser Phe Ala Glu Met Tyr Gly Trp Arg Ala Gly Glu
            645                 650                 655 tct ttg aaa acg ttg gat ctg aaa ccg gaa aaa tcc ttt aat aga gag    2736
Ser Leu Lys Thr Leu Asp Leu Lys Pro Glu Lys Ser Phe Asn Arg Glu
660                 665                 670 gca ggt att gta ttt aaa ggg gac ttc ggc aat ttg gaa gcc agc tat    2784
Ala Gly Ile Val Phe Lys Gly Asp Phe Gly Asn Leu Glu Ala Ser Tyr
        675                 680                 685 ttc aac aat gcc tat cgc gac ctg att gca ttc ggt tat gaa acc cga    2832
Phe Asn Asn Ala Tyr Arg Asp Leu Ile Ala Phe Gly Tyr Glu Thr Arg
    690                 695                 700 act caa aac ggg caa act tcg gct tct ggc gac ccc gga tac cga aat    2880
Thr Gln Asn Gly Gln Thr Ser Ala Ser Gly Asp Pro Gly Tyr Arg Asn
705                 710                 715                 720 ggc cca aaa tgc acg gta gta gcc ggt atc aat att ttg ggt aaa atc    2928
Gly Pro Lys Cys Thr Val Val Ala Gly Ile Asn Ile Leu Gly Lys Ile
            725                 730                 735 gat tgg cac ggc gta tgg ggc ggg ttg ccg gac ggg ttg tat tcc acg    2976
Asp Trp His Gly Val Trp Gly Gly Leu Pro Asp Gly Leu Tyr Ser Thr
        740                 745                 750 ctt gcc tat aac cgt atc aag gtc aaa gat gcc gat ata cgc gcc gac    3024
Leu Ala Tyr Asn Arg Ile Lys Val Lys Asp Ala Asp Ile Arg Ala Asp
    755                 760                 765 agg acg ttt gta act tca tat ctc ttt gat gcc gtc caa cct tca cga    3072
Arg Thr Phe Val Thr Ser Tyr Leu Phe Asp Ala Val Gln Pro Ser Arg
770                 775                 780 tat gta ttg ggt ttg ggt tac gac cat cct gac gga ata tgg ggc atc    3120
Tyr Val Leu Gly Leu Gly Tyr Asp His Pro Asp Gly Ile Trp Gly Ile
785                 790                 795                 800 aat acg atg ttt act tat tcc aag gca aaa tct gtt gac gaa ctg ctc    3168
Asn Thr Met Phe Thr Tyr Ser Lys Ala Lys Ser Val Asp Glu Leu Leu
            805                 810                 815 ggc agc cag gcg ctg ttg aac ggt aat gcc aat gct aaa aaa gca gca    3216
Gly Ser Gln Ala Leu Leu Asn Gly Asn Ala Asn Ala Lys Lys Ala Ala
        820                 825                 830 tca cgg cgg acg cgg cct tgg tat gtt acg gat gtt tcc gga tat tac    3264
Ser Arg Arg Thr Arg Pro Trp Tyr Val Thr Asp Val Ser Gly Tyr Tyr
    835                 840                 845 aat atc aag aaa cac ctg acc ctg cgc gca ggt gta tac aac ctc ctc    3312
Asn Ile Lys Lys His Leu Thr Leu Arg Ala Gly Val Tyr Asn Leu Leu
850                 855                 860 aac tac cgc tat gtt act tgg gaa aat gtg cgg caa act gcc ggc ggc    3360
Asn Tyr Arg Tyr Val Thr Trp Glu Asn Val Arg Gln Thr Ala Gly Gly
865                 870                 875                 880 gca gtc aac caa cac aaa aat gtc ggc gtt tac aac cga tat gcc gcc    3408
Ala Val Asn Gln His Lys Asn Val Gly Val Tyr Asn Arg Tyr Ala Ala
            885                 890                 895 ccc ggc cga aac tac aca ttt agc ttg gaa atg aag ttt taaacgtcca    3457
Pro Gly Arg Asn Tyr Thr Phe Ser Leu Glu Met Lys Phe
        900                 905 aacgccgcaa atgccgtctg aaaggcttca gacggcattt tttacacaat tcccaccgtt  3517
tcccatcatc cccgatacac                                              3537

<210> SEQ ID NO 4
<211> LENGTH: 909
<212> TYPE: PRT
<213> ORGANISM: Neisseria meningitidis
```

<400> SEQUENCE: 4

```
Met Gln Gln Gln His Leu Phe Arg Leu Asn Ile Leu Cys Leu Ser Leu
  1               5                  10                  15

Met Thr Ala Leu Pro Val Tyr Ala Glu Asn Val Gln Ala Glu Gln Ala
             20                  25                  30

Gln Glu Lys Gln Leu Asp Thr Ile Gln Val Lys Ala Lys Lys Gln Lys
         35                  40                  45

Thr Arg Arg Asp Asn Glu Val Thr Gly Leu Gly Lys Leu Val Lys Ser
     50                  55                  60

Ser Asp Thr Leu Ser Lys Glu Gln Val Leu Asn Ile Arg Asp Leu Thr
 65                  70                  75                  80

Arg Tyr Asp Pro Gly Ile Ala Val Val Glu Gln Gly Arg Gly Ala Ser
                 85                  90                  95

Ser Gly Tyr Ser Ile Arg Gly Met Asp Lys Asn Arg Val Ser Leu Thr
            100                 105                 110

Val Asp Gly Val Ser Gln Ile Gln Ser Tyr Thr Ala Gln Ala Ala Leu
        115                 120                 125

Gly Gly Thr Arg Thr Ala Gly Ser Ser Gly Ala Ile Asn Glu Ile Glu
    130                 135                 140

Tyr Glu Asn Val Lys Ala Val Glu Ile Ser Lys Gly Ser Asn Ser Ser
145                 150                 155                 160

Glu Tyr Gly Asn Gly Ala Leu Ala Gly Ser Val Ala Phe Gln Thr Lys
                165                 170                 175

Thr Ala Ala Asp Ile Ile Gly Glu Gly Lys Gln Trp Gly Ile Gln Ser
            180                 185                 190

Lys Thr Ala Tyr Ser Gly Lys Asp His Ala Leu Thr Gln Ser Leu Ala
        195                 200                 205

Leu Ala Gly Arg Ser Gly Gly Ala Glu Ala Leu Leu Ile Tyr Thr Lys
    210                 215                 220

Arg Arg Gly Arg Glu Ile His Ala His Lys Asp Ala Gly Lys Gly Val
225                 230                 235                 240

Gln Ser Phe Asn Arg Leu Val Leu Asp Glu Asp Lys Lys Glu Gly Gly
                245                 250                 255

Ser Gln Ser Asp Ile Ser Leu Cys Glu Glu Cys His Asn Gly Tyr
            260                 265                 270

Ala Ala Cys Lys Asn Lys Leu Lys Glu Asp Ala Ser Val Lys Asp Glu
        275                 280                 285

Arg Lys Thr Val Ser Thr Gln Asp Tyr Thr Gly Ser Asn Arg Leu Leu
    290                 295                 300

Ala Asn Pro Leu Glu Tyr Gly Ser Gln Ser Trp Leu Phe Arg Pro Gly
305                 310                 315                 320

Trp His Leu Asp Asn Arg His Tyr Val Gly Ala Val Leu Glu Arg Thr
                325                 330                 335

Gln Gln Thr Phe Asp Thr Arg Asp Met Thr Val Pro Ala Tyr Phe Thr
            340                 345                 350

Ser Glu Asp Tyr Val Pro Gly Ser Leu Lys Gly Leu Gly Lys Tyr Ser
        355                 360                 365

Gly Asp Asn Lys Ala Glu Arg Leu Phe Val Gln Gly Glu Gly Ser Thr
    370                 375                 380

Leu Gln Gly Ile Gly Tyr Gly Thr Gly Val Phe Tyr Asp Glu Arg His
385                 390                 395                 400

Thr Lys Asn Arg Tyr Gly Val Glu Tyr Val Tyr His Asn Ala Asp Lys
                405                 410                 415
```

```
Asp Thr Trp Ala Asp Tyr Ala Arg Leu Ser Tyr Asp Arg Gln Gly Ile
            420                 425                 430

Asp Leu Asp Asn Arg Leu Gln Gln Thr His Cys Ser His Asp Gly Ser
        435                 440                 445

Asp Lys Asn Cys Arg Pro Asp Gly Asn Lys Pro Tyr Ser Phe Tyr Lys
    450                 455                 460

Ser Asp Arg Met Ile Tyr Glu Glu Ser Arg Asn Leu Phe Gln Ala Val
465                 470                 475                 480

Phe Lys Lys Ala Phe Asp Thr Ala Lys Ile Arg His Asn Leu Ser Ile
                485                 490                 495

Asn Leu Gly Tyr Asp Arg Phe Lys Ser Gln Leu Ser His Ser Asp Tyr
            500                 505                 510

Tyr Leu Gln Asn Ala Val Gln Ala Tyr Asp Leu Ile Thr Pro Lys Lys
        515                 520                 525

Pro Pro Phe Pro Asn Gly Ser Lys Asp Asn Pro Tyr Arg Val Ser Ile
    530                 535                 540

Gly Lys Thr Thr Val Asn Thr Ser Pro Ile Pro Gly Phe Gly Asn Asn
545                 550                 555                 560

Thr Tyr Thr Asp Cys Thr Pro Arg Asn Ile Gly Gly Asn Gly Tyr Tyr
                565                 570                 575

Ala Ala Val Gln Asp Asn Val Arg Leu Gly Arg Trp Ala Asp Val Gly
            580                 585                 590

Ala Gly Ile Arg Tyr Asp Tyr Arg Ser Thr His Ser Glu Asp Lys Ser
        595                 600                 605

Val Ser Thr Gly Thr His Arg Asn Leu Ser Trp Asn Ala Gly Val Val
    610                 615                 620

Leu Lys Pro Phe Thr Trp Met Asp Leu Thr Tyr Arg Ala Ser Thr Gly
625                 630                 635                 640

Phe Arg Leu Pro Ser Phe Ala Glu Met Tyr Gly Trp Arg Ala Gly Glu
                645                 650                 655

Ser Leu Lys Thr Leu Asp Leu Lys Pro Glu Lys Ser Phe Asn Arg Glu
            660                 665                 670

Ala Gly Ile Val Phe Lys Gly Asp Phe Gly Asn Leu Glu Ala Ser Tyr
        675                 680                 685

Phe Asn Asn Ala Tyr Arg Asp Leu Ile Ala Phe Gly Tyr Glu Thr Arg
    690                 695                 700

Thr Gln Asn Gly Gln Thr Ser Ala Ser Gly Asp Pro Gly Tyr Arg Asn
705                 710                 715                 720

Gly Pro Lys Cys Thr Val Val Ala Gly Ile Asn Ile Leu Gly Lys Ile
                725                 730                 735

Asp Trp His Gly Val Trp Gly Gly Leu Pro Asp Gly Leu Tyr Ser Thr
            740                 745                 750

Leu Ala Tyr Asn Arg Ile Lys Val Lys Asp Ala Asp Ile Arg Ala Asp
        755                 760                 765

Arg Thr Phe Val Thr Ser Tyr Leu Phe Asp Ala Val Gln Pro Ser Arg
    770                 775                 780

Tyr Val Leu Gly Leu Gly Tyr Asp His Pro Asp Gly Ile Trp Gly Ile
785                 790                 795                 800

Asn Thr Met Phe Thr Tyr Ser Lys Ala Lys Ser Val Asp Glu Leu Leu
                805                 810                 815

Gly Ser Gln Ala Leu Leu Asn Gly Asn Ala Asn Ala Lys Lys Ala Ala
            820                 825                 830
```

```
                                      -continued
Ser Arg Arg Thr Arg Pro Trp Tyr Val Thr Asp Val Ser Gly Tyr Tyr
        835                 840                 845

Asn Ile Lys Lys His Leu Thr Leu Arg Ala Gly Val Tyr Asn Leu Leu
850                 855                 860

Asn Tyr Arg Tyr Val Thr Trp Glu Asn Val Arg Gln Thr Ala Gly Gly
865                 870                 875                 880

Ala Val Asn Gln His Lys Asn Val Gly Val Tyr Asn Arg Tyr Ala Ala
                885                 890                 895

Pro Gly Arg Asn Tyr Thr Phe Ser Leu Glu Met Lys Phe
                900                 905
```